US009655555B2

(12) United States Patent
Burnett et al.

(10) Patent No.: US 9,655,555 B2
(45) Date of Patent: *May 23, 2017

(54) SENSING FOLEY CATHETER

(75) Inventors: Daniel R. Burnett, San Francisco, CA (US); Greg Lee, San Francisco, CA (US); Richard W. O'Connor, Redwood City, CA (US); Brett Mensh, San Rafael, CA (US)

(73) Assignee: Potrero Medical, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/414,011

(22) Filed: Mar. 7, 2012

(65) Prior Publication Data

US 2013/0030262 A1   Jan. 31, 2013

Related U.S. Application Data

(60) Provisional application No. 61/464,619, filed on Mar. 7, 2011, provisional application No. 61/628,534, filed (Continued)

(51) Int. Cl.
*A61B 5/00*        (2006.01)
*A61B 5/0205*    (2006.01)

(Continued)

(52) U.S. Cl.
CPC .......... *A61B 5/205* (2013.01); *A61B 5/0215* (2013.01); *A61B 5/207* (2013.01); *A61B 5/6852* (2013.01);

(Continued)

(58) Field of Classification Search
None
See application file for complete search history.

(56) References Cited

U.S. PATENT DOCUMENTS 3,326,207 A    6/1967  Egan
4,077,394 A  *  3/1978  McCurdy ..................... 600/18

(Continued)

FOREIGN PATENT DOCUMENTS

WO    WO 2006/060248           6/2006
WO    WO 2007018963 A2  *  2/2007  .............. A61B 5/03

(Continued)

OTHER PUBLICATIONS

Addington, Intra-abdominal Pressures during Voluntary and Reflex Cough, Cough 2008, 4:2.*

(Continued)

*Primary Examiner* — Gary Jackson
*Assistant Examiner* — Manolis Pahakis
(74) *Attorney, Agent, or Firm* — Levine Bagade Han LLP

(57) ABSTRACT

Foley type catheter embodiments for sensing physiologic data from a urinary tract of a patient are disclosed. The system includes the catheter and a data processing apparatus and methods for sensing physiologic data from the urinary tract. Embodiments may also include a pressure sensor having a pressure interface at a distal end of the catheter, a pressure transducer at a proximal, and a fluid column disposed between the pressure interface and transducer. When the distal end is residing in the bladder, the pressure transducer can transduce pressure impinging on it into a chronological pressure profile, which can be processed by the data processing apparatus into one or more distinct physiologic pressure profiles, for example, peritoneal pressure, respiratory rate, and cardiac rate. At a sufficiently high data-sampling rate, these physiologic data may further include relative pulmonary tidal volume, cardiac output, relative cardiac output, and absolute cardiac stroke volume.

24 Claims, 15 Drawing Sheets

Related U.S. Application Data on Nov. 2, 2011, provisional application No. 61/583,258, filed on Jan. 5, 2012.

(51) Int. Cl.
| | |
|---|---|
| *A61B 5/0215* | (2006.01) |
| *A61B 5/20* | (2006.01) |
| *A61M 25/00* | (2006.01) |
| *A61B 5/024* | (2006.01) |
| *A61B 5/029* | (2006.01) |
| *A61B 5/0476* | (2006.01) |
| *A61B 5/08* | (2006.01) |
| *A61B 10/00* | (2006.01) |
| *A61M 25/04* | (2006.01) |

(52) U.S. Cl.
CPC ......... *A61M 25/0017* (2013.01); *A61B 5/024* (2013.01); *A61B 5/029* (2013.01); *A61B 5/0476* (2013.01); *A61B 5/0816* (2013.01); *A61B 5/4839* (2013.01); *A61B 10/007* (2013.01); *A61B 2562/0247* (2013.01); *A61M 25/04* (2013.01); *A61M 2025/0003* (2013.01)

(56) References Cited

U.S. PATENT DOCUMENTS

| | | | |
|---|---|---|---|
| 4,413,633 A | 11/1983 | Yanda | |
| 4,502,490 A * | 3/1985 | Evans et al. ................. | 600/593 |
| 4,600,015 A * | 7/1986 | Evans et al. ................. | 600/593 |
| 4,712,566 A * | 12/1987 | Hok ............................. | 600/561 |
| 4,841,981 A * | 6/1989 | Tanabe et al. ............... | 600/505 |
| 5,035,231 A * | 7/1991 | Kubokawa et al. ......... | 600/109 |
| 5,048,532 A * | 9/1991 | Hickey ........................ | 600/488 |
| 5,133,358 A * | 7/1992 | Gustafson .............. | G01L 27/005 |
| | | | 600/488 |
| 5,158,529 A * | 10/1992 | Kanai ..................... | A61M 1/1086 |
| | | | 600/18 |
| 5,171,299 A | 12/1992 | Heitzmann et al. ..... | 604/100.03 |
| 5,220,927 A | 6/1993 | Astrahan et al. | |
| 5,240,675 A | 8/1993 | Wilk et al. | |
| 5,257,630 A * | 11/1993 | Broitman .............. | A61B 5/0215 |
| | | | 338/42 |
| 5,263,485 A * | 11/1993 | Hickey ................. | A61B 5/0215 |
| | | | 600/486 |
| 5,344,435 A | 9/1994 | Turner et al. | |
| 5,389,217 A | 2/1995 | Singer | |
| 5,398,692 A * | 3/1995 | Hickey ....................... | 600/486 |
| 5,413,558 A * | 5/1995 | Paradis ................... | 604/101.05 |
| 5,425,362 A | 6/1995 | Siker et al. | |
| 5,427,114 A * | 6/1995 | Colliver et al. ............. | 600/561 |
| 5,431,628 A * | 7/1995 | Millar ...................... | 604/100.01 |
| 5,433,216 A * | 7/1995 | Sugrue et al. .............. | 600/591 |
| 5,517,998 A * | 5/1996 | Madison .................. | A61B 5/03 |
| | | | 600/473 |
| 5,570,671 A | 11/1996 | Hickey | |
| 5,573,007 A * | 11/1996 | Bobo, Sr. .............. | A61B 5/0215 |
| | | | 600/561 |
| 5,678,570 A * | 10/1997 | Manning ............... | A61M 1/3621 |
| | | | 128/897 |
| 5,788,642 A * | 8/1998 | Hamatake ............. | A61B 5/031 |
| | | | 600/486 |
| 5,865,801 A * | 2/1999 | Houser ...................... | 604/103.07 |
| 5,902,248 A * | 5/1999 | Millar et al. ................ | 600/485 |
| 5,916,153 A | 6/1999 | Rhea, Jr. | |
| 5,921,935 A * | 7/1999 | Hickey ........................ | 600/485 |
| 5,984,879 A * | 11/1999 | Wallace ................ | A61B 5/035 |
| | | | 600/585 |
| 6,001,600 A | 12/1999 | Hodgson et al. ............. | 435/69.3 |
| 6,083,215 A * | 7/2000 | Milavetz ..................... | 604/509 |
| 6,149,578 A * | 11/2000 | Downey et al. ............. | 600/18 |
| 6,287,253 B1 | 9/2001 | Ortega et al. | |
| 6,299,583 B1 * | 10/2001 | Eggers .................. | A61B 5/0215 |
| | | | 600/341 |
| 6,322,514 B1 * | 11/2001 | Holte ..................... | A61B 5/029 |
| | | | 600/481 |
| 6,434,418 B1 | 8/2002 | Neal et al. | |
| 6,447,462 B1 * | 9/2002 | Wallace et al. .............. | 600/561 |
| 6,511,412 B1 * | 1/2003 | Freed .................... | A61M 1/1072 |
| | | | 600/17 |
| 6,602,243 B2 | 8/2003 | Noda | |
| 6,616,597 B2 * | 9/2003 | Schock et al. ................. | 600/18 |
| 6,648,906 B2 | 11/2003 | Lasheras et al. | |
| 6,666,828 B2 | 12/2003 | Greco et al. | |
| 6,912,416 B2 | 6/2005 | Rosenblatt | |
| 6,916,283 B2 | 7/2005 | Tracey et al. | |
| 6,918,924 B2 | 7/2005 | Lasheras | |
| 6,931,276 B2 | 8/2005 | Streng et al. | |
| 6,997,884 B2 | 2/2006 | Ulmsten et al. | |
| 7,004,899 B2 | 2/2006 | Tracey | |
| 7,025,718 B2 | 4/2006 | Williams | |
| 7,052,452 B2 | 5/2006 | Ulmsten et al. | |
| 7,112,177 B2 * | 9/2006 | Christensen et al. ......... | 600/561 |
| 7,252,631 B2 | 8/2007 | Tracey | |
| 7,255,673 B2 | 8/2007 | Ulmsten et al. | |
| 7,381,190 B2 * | 6/2008 | Sugrue et al. ................ | 600/561 |
| 7,527,599 B2 * | 5/2009 | Hickey ....................... | 600/508 |
| 7,644,722 B2 * | 1/2010 | Christensen et al. ......... | 137/107 |
| 7,726,328 B2 | 6/2010 | Christensen et al. | |
| 7,892,181 B2 * | 2/2011 | Christensen et al. ......... | 600/561 |
| 8,052,671 B2 * | 11/2011 | Christensen et al. ......... | 604/540 |
| 8,116,838 B2 * | 2/2012 | Gaspard et al. .............. | 600/322 |
| 8,337,411 B2 * | 12/2012 | Nishtala et al. .............. | 600/561 |
| 8,366,639 B2 * | 2/2013 | Toyota et al. ................. | 600/587 |
| 8,396,537 B2 * | 3/2013 | Balji et al. ................... | 600/509 |
| 8,403,884 B2 | 3/2013 | Nishtala | |
| 2001/0020162 A1 * | 9/2001 | Mosel et al. ................. | 604/544 |
| 2001/0035046 A1 * | 11/2001 | Williams .......................... | 73/40 |
| 2002/0049425 A1 * | 4/2002 | Mosel et al. ................. | 604/544 |
| 2002/0066458 A1 * | 6/2002 | Aliberto et al. .............. | 128/898 |
| 2002/0077680 A1 | 6/2002 | Noda | |
| 2003/0114835 A1 | 6/2003 | Noda | |
| 2004/0097813 A1 * | 5/2004 | Williams ............ | A61B 1/00082 |
| | | | 600/485 |
| 2004/0167415 A1 * | 8/2004 | Gelfand et al. .............. | 600/500 |
| 2004/0236395 A1 * | 11/2004 | Iaizzo et al. ................. | 607/116 |
| 2005/0075531 A1 * | 4/2005 | Loeb ..................... | A61H 9/0078 |
| | | | 600/17 |
| 2005/0209524 A1 * | 9/2005 | Donaldson ............. | A61B 5/042 |
| | | | 600/510 |
| 2005/0288603 A1 * | 12/2005 | Goping ........................ | 600/561 |
| 2006/0100743 A1 * | 5/2006 | Townsend .......... | A61B 5/14507 |
| | | | 700/266 |
| 2006/0116601 A1 | 6/2006 | Glocker | |
| 2006/0178571 A1 * | 8/2006 | Barnett ....................... | 600/311 |
| 2006/0234383 A1 * | 10/2006 | Gough ............................ | 436/63 |
| 2006/0275907 A1 | 12/2006 | Glocker | |
| 2006/0287604 A1 | 12/2006 | Hickey | |
| 2007/0038143 A1 * | 2/2007 | Christensen et al. ......... | 600/561 |
| 2007/0083126 A1 * | 4/2007 | Marko et al. ................. | 600/505 |
| 2007/0225584 A1 * | 9/2007 | Gravenstein et al. ........ | 600/376 |
| 2007/0255167 A1 * | 11/2007 | Christensen et al. ......... | 600/561 |
| 2007/0270699 A1 * | 11/2007 | Crabtree et al. ............. | 600/500 |
| 2008/0103408 A1 * | 5/2008 | Denton et al. ................ | 600/549 |
| 2008/0140000 A1 * | 6/2008 | Shuros ............... | A61N 1/36007 |
| | | | 604/96.01 |
| 2008/0262418 A1 * | 10/2008 | Burnett ................. | A61M 5/142 |
| | | | 604/66 |
| 2009/0043184 A1 * | 2/2009 | Fjield ................... | A61B 5/145 |
| | | | 600/366 |
| 2009/0076573 A1 * | 3/2009 | Burnett ..................... | A61F 7/12 |
| | | | 607/105 |
| 2009/0120439 A1 * | 5/2009 | Goebel ....................... | 128/204.21 |
| 2009/0221933 A1 | 9/2009 | Nishtala et al. | |
| 2009/0306588 A1 * | 12/2009 | Nguyen et al. ............. | 604/96.01 |
| 2009/0312740 A1 * | 12/2009 | Kim et al. .................... | 604/500 |
| 2010/0010552 A1 | 1/2010 | Wilson et al. | |
| 2010/0030190 A1 * | 2/2010 | Singh ...................... | A61F 7/123 |
| | | | 604/516 |
| 2010/0057046 A1 * | 3/2010 | Stevens (nee Webber) et al. ............................ | 604/507 |

(56) References Cited

U.S. PATENT DOCUMENTS

| | | | |
|---|---|---|---|
| 2010/0121159 A1* | 5/2010 | Burnett | A61B 5/01 600/301 |
| 2010/0121220 A1 | 5/2010 | Nishtala | |
| 2010/0130880 A1 | 5/2010 | Li | |
| 2010/0204765 A1* | 8/2010 | Hall | A61F 7/12 607/105 |
| 2010/0228148 A1 | 9/2010 | Kim | |
| 2010/0249663 A1* | 9/2010 | Nishtala | 600/587 |
| 2010/0286559 A1* | 11/2010 | Paz | A61B 5/14507 600/581 |
| 2011/0040211 A1* | 2/2011 | Addington | A61B 5/04882 600/587 |
| 2011/0046653 A1* | 2/2011 | Addington | A61B 5/04882 606/196 |
| 2011/0071482 A1 | 3/2011 | Selevan | |
| 2011/0082554 A1* | 4/2011 | Glazer et al. | 623/17.16 |
| 2011/0144423 A1 | 6/2011 | Tong et al. | |
| 2012/0095537 A1* | 4/2012 | Hall | A61F 7/12 607/105 |
| 2013/0030262 A1* | 1/2013 | Burnett et al. | 600/309 |
| 2013/0066166 A1 | 3/2013 | Burnett et al. | |
| 2013/0231584 A1* | 9/2013 | Burnett | A61B 5/036 600/561 |

FOREIGN PATENT DOCUMENTS

| | | | | |
|---|---|---|---|---|
| WO | WO 2008097609 A2 * | 8/2008 | | A61B 17/34 |
| WO | WO 2008103625 A2 * | 8/2008 | | A61M 1/00 |
| WO | WO 2008117574 A1 * | 10/2008 | | A61B 5/22 |
| WO | WO 2009055435 A1 * | 4/2009 | | A61B 5/03 |
| WO | WO 2012/122267 | 9/2012 | | |

OTHER PUBLICATIONS

Marquet Getinge Group, Background of Zeroing/Calibration Process of a Pressure Measurement Device, 2010.*

Balogh et al., Continuous intra-abdominal pressure measurement technique, The American Journal of Surgery 188 (2004) 679-684.*

* cited by examiner

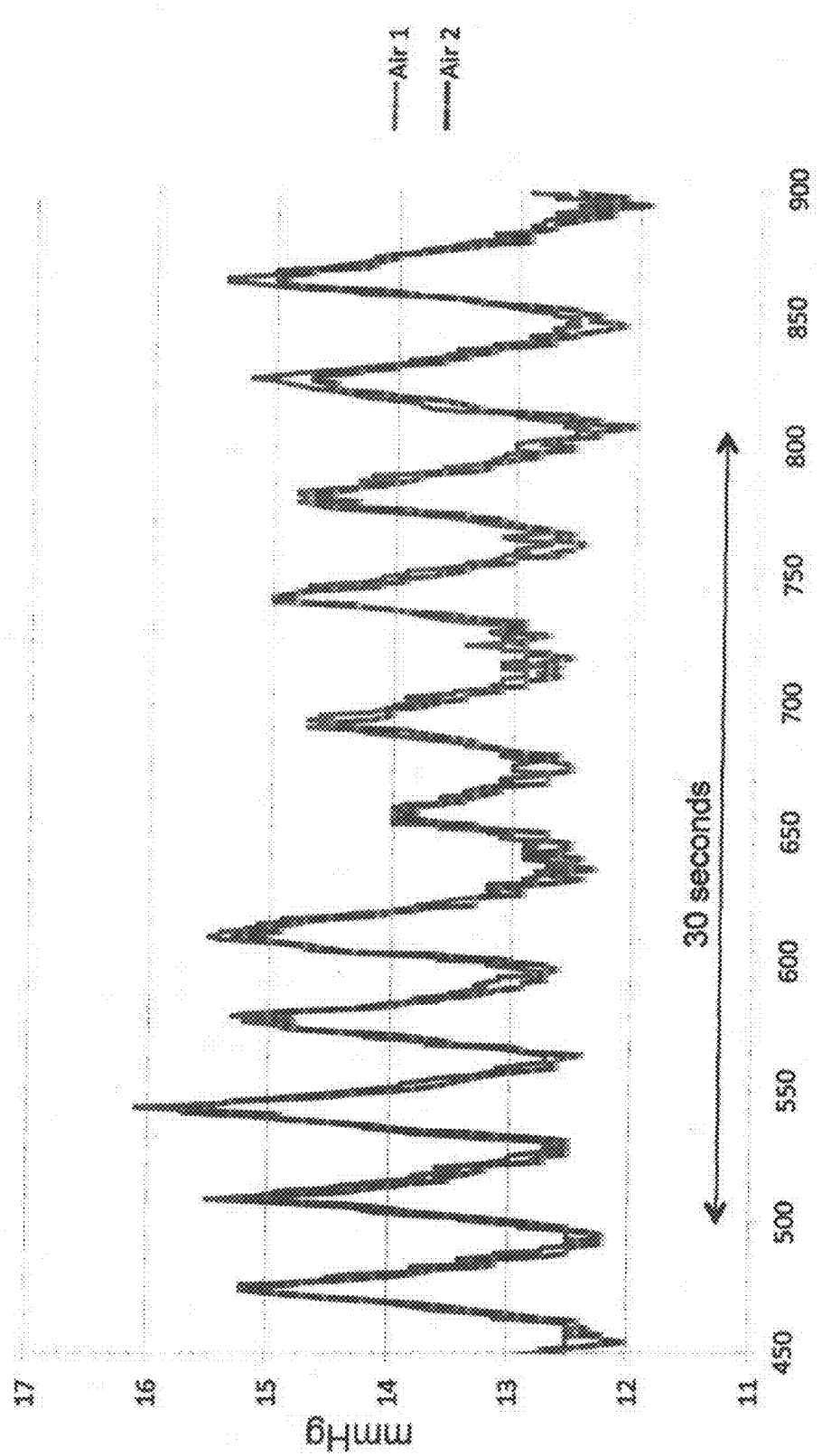

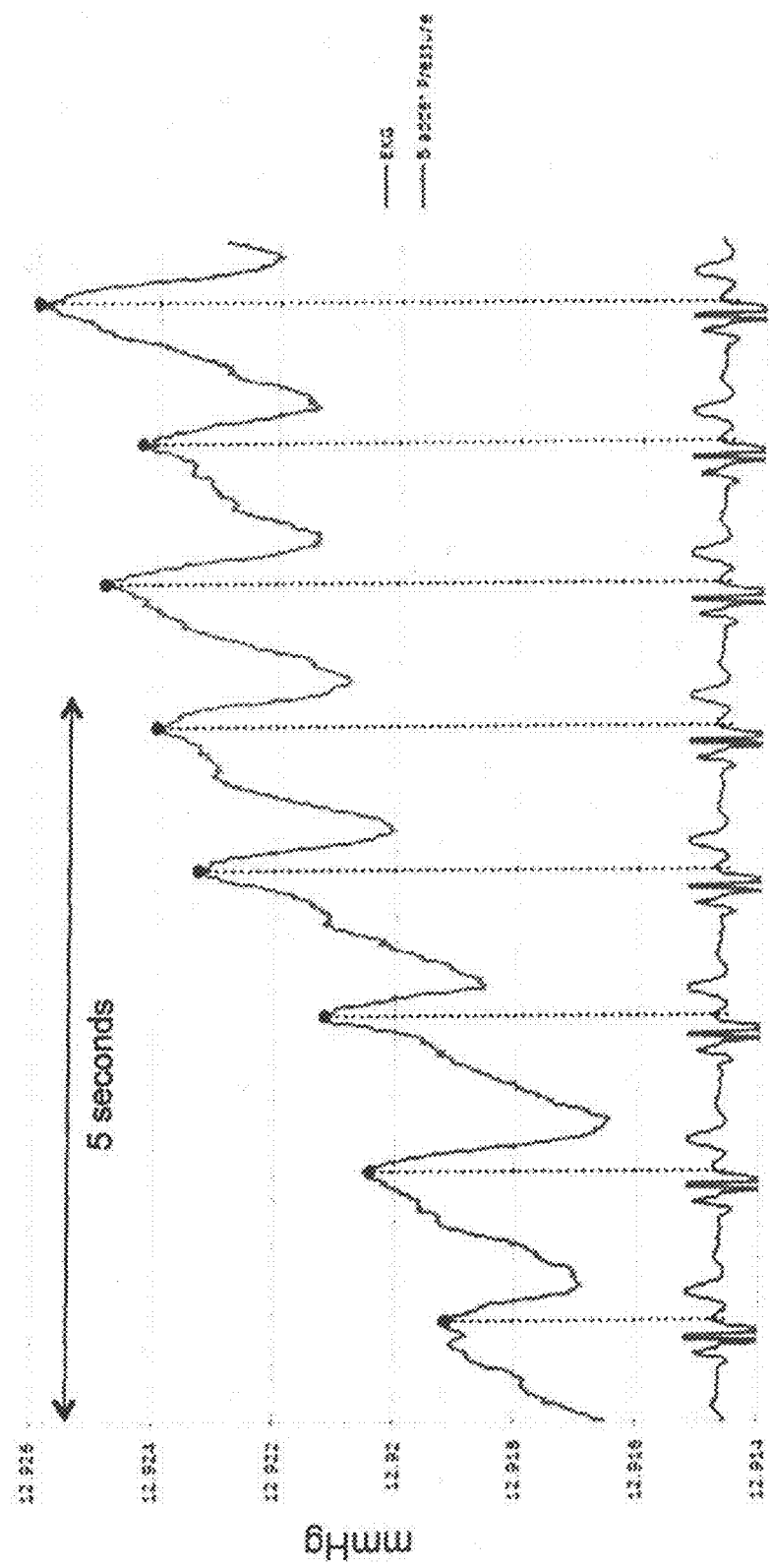

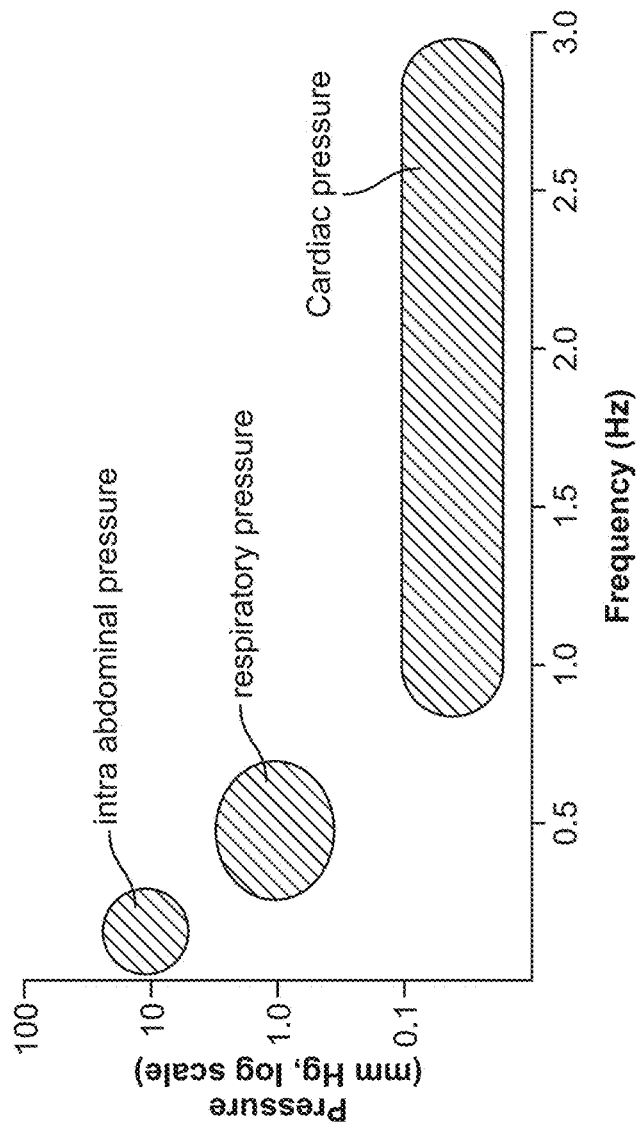

Method of Monitoring Pressure-based Physiologic Data

Dynamic pressure in the bladder / intraabdominal cavity  High fidelity pressure profile generated  Pressure transducer converts high fidelity pressure to high fidelity electrical signal  Electrical signal profile processed to determine:
1 peritoneal pressure
2 respiratory rate
3 cardiac rate
4 relative cardiac output
5 patient motion or activity

Fig. 13

SENSING FOLEY CATHETER

CROSS-REFERENCE TO RELATED APPLICATIONS

This application claims the benefit of U.S. Provisional Application No. 61/464,619, filed Mar. 7, 2011, U.S. Provisional Application No. 61/628,534, filed Nov. 2, 2011, and U.S. Provisional Application No. 61/583,258, filed Jan. 5, 2012. Each of these applications is incorporated herein by reference in its entirety.

TECHNICAL FIELD OF THE INVENTION

The disclosed technology relates to the field of medical devices, in particular devices capable of sensing physiologic data based on sensors incorporated into a catheter adapted to reside in the a urinary tract of a patient.

INCORPORATION BY REFERENCE

All publications and patent applications mentioned in this specification are herein incorporated by reference to the same extent as if each such individual publication or patent application were specifically and individually indicated to be so incorporated by reference.

BACKGROUND OF THE INVENTION

The Foley catheter, named for Dr. Frederick Foley who first described a self-retaining balloon catheter in 1929, has been in use since the 1930's, in a form nearly identical to its early models. In its most basic form, a Foley catheter has a proximal portion that remains outside the body, a length that traverses the urethra, and a distal end that resides in the urinary bladder. The Foley catheter is held in place by an inflatable balloon that stabilizes the device in place, and prevents inadvertent withdrawal from the bladder. A typical Foley catheter includes at least two lumens along its length; one lumen serves as a conduit that drains the bladder, and the second lumen serves as an air conduit that allows the balloon to be controllably inflated and deflated.

Various developments have added diagnostic functionality to Foley type catheters, including the ability to measure pressure and temperature. For example, U.S. Pat. No. 5,389,217 of Singer discloses a catheter with oxygen sensing capability. U.S. Pat. No. 5,916,153 of Rhea and U.S. Pat. No. 6,434,418 of Neal both disclose a pressure sensor associated with a Foley type catheter. U.S. Pat. No. 6,602,243 to Noda discloses a temperature sensor associated with a Foley type catheter.

The Foley catheter, widespread in use, having a low cost, and easily put in place by health care professionals may offer still further opportunity as a vehicle for deriving critical diagnostic information. The technology disclosed herein provides for the delivery of highly resolved and previously unavailable diagnostic information, as may be derived from a Foley catheter with pressure sensing capability.

SUMMARY OF THE INVENTION

The disclosed technology relates to a Foley type catheter for sensing physiologic data from the urinary tract of a patient, the physiologic data particularly including those gathered by high fidelity pressure sensing and transduction into signals suitable for processing. In some embodiments, the pressure-sensing Foley type catheter may further be enabled to sense temperature and analytes of clinical significance.

Embodiments of the Foley type catheter include a pressure sensor having a pressure interface disposed at a distal end of the catheter, a pressure transducer at a proximal end of the catheter, and a fluid column disposed between the pressure interface and the pressure transducer. When an embodiment of catheter is appropriately or functionally inserted into the urinary tract of a patient and the distal end is residing in the bladder, the pressure transducer can transduce pressure impinging on it from the pressure interface into a chronological pressure profile. The pressure profile has sufficient resolution to be processed into one or more distinct physiologic pressure profiles, including peritoneal pressure, respiratory rate, and cardiac rate.

In some particular embodiments of the Foley type catheter, the pressure profile generated by the pressure sensor has sufficient resolution such that, when sampled by a transducer at a frequency of at least about 1 Hz, it can be processed to yield a relative pulmonary tidal volume profile. In still further embodiments of the Foley type catheter, the pressure profile generated by the pressure sensor has sufficient resolution such that, when sampled by a transducer at a frequency of at least about 5 Hz, it can be processed to yield physiologic pressure profiles selected from a group consisting of cardiac output, relative cardiac output, and absolute cardiac stroke volume.

In various embodiments of the catheter, the fluid within the fluid column may include a gas, such as air or carbon dioxide, or it may include a liquid. In some embodiments wherein the fluid column includes a liquid, such liquid may include urine, as sourced from the bladder.

In various embodiments of the catheter, the pressure interface may include an elastic membrane or a substantially inelastic membrane. In some embodiments, the pressure interface is substantially homogeneous across its surface area. In other embodiments, the pressure interface can be heterogeneous, having regions that vary in composition or thickness, or having features that provide an elasticity bias.

In particular embodiments of the catheter, the pressure interface includes an expandable balloon. Such an expandable balloon may include either an elastic membrane or a substantially inelastic membrane. Embodiments of the balloon, particularly those having an inelastic membrane, upon expansion, the balloon has a volume in the range of about 0.1 cc to about 2 cc. Other embodiments of the balloon, upon expansion, may have larger volumes, for example, in a range of about 2 cc to about 5 cc, or in a range of about 5 cc to about 250 cc, a volume that is greater than 250 cc. In another aspect, upon inflation, embodiments of the balloon may have a diameter that ranges between about 6 mm and 8 mm.

In various embodiments of the catheter, the pressure interface includes a membrane arranged across an opening. In such embodiments, the membrane is sufficiently elastic to respond to an internal-external pressure differential across its surface.

In some embodiments, the Foley type catheter further includes a temperature sensor to monitor a body core temperature of the patient. In these embodiments, the physiologic data from the temperature sensor in the system may be used to monitor body temperature and to feedback control delivery of a hypothermic treatment regimen. Temperatures sensors appropriate for the Foley type catheter may be of any conventional type, including by way of example, a thermistor, a thermocouple, or an optical temperature sensor.

In some embodiments, the Foley type catheter further includes one or more analyte sensors. Analyte sensors included in the scope of the disclosed technology include sensors for analytes of any clinical significance. For broad examples, such analytes may include any analyte selected from a group including pH, a gas, an electrolyte, a metabolic substrate, a metabolite, an enzyme, or a hormone. By way of particular examples, such analyte sensor may be able to sense any of a metabolic substrate or a metabolite, the analytes may include glucose or lactic acid. By way of example of a hormone, the analyte may include cortisol.

In some embodiments, the Foley type catheter further includes one or more electrodes arranged as electrical activity sensors. Such electrical activity sensors may deliver physiologic data that can be transformed to yield an electrocardiogram (EKG) or an electrogastrogram (EGG).

In some embodiments, the Foley type catheter further includes a light source and a light sensor, the sensor configured to capture light emitted from the light source. In some embodiments, by way of example, the light source and the light sensor may be configured to operate as a pulse oximeter, the light sensor being able to deliver a signal that can be transduced into a pulse rate. In another example, the light source and the light sensor may be configured to operate as an analyte sensor.

Some embodiments of the Foley type catheter may further include an expandable pressure-delivery balloon disposed on the catheter so as, upon expansion, to contact a wall of the bladder or the urethra; and a light source and a light sensor disposed proximate the tissue-compressing balloon. The pressure delivery balloon, the light source, and the light sensor may be arranged such that when the expandable pressure balloon is expanded so as to blanche a tissue surrounding it as detected by the light sensor, a light-based signal from the light sensor may be processed to yield a perfusion pressure on a urinary bladder wall or a urethra.

Some embodiments of the disclosed technology relate to a Foley type catheter for sensing pressure-based physiologic data from the urinary tract of a patient having a pressure sensor that includes a pressure interface and a transducer, the sensor not including a pressure-transmitting column. These embodiments typically have a pressure sensing mechanism or transducer proximate the pressure interface. Such pressure sensors may include, by way of example, any of a piezoelectric electric mechanism, an optical sensing mechanism, a microelectricalmechanical (MEMS) mechanism, or an acoustic wave sensing mechanism. When the catheter is appropriately or functionally inserted into the urinary tract and the distal end is residing in the bladder, the pressure sensor can transduce pressure impinging on it from the pressure interface into a chronological pressure profile, the pressure profile having sufficient resolution to allow differentiation into one or more physiologic pressure profiles selected from the group consisting of peritoneal pressure, respiratory rate, and cardiac rate.

The disclosed technology relates to a Foley type catheter for sensing pressure-based physiologic data from the urinary tract of a patient, as summarized above, but further being enabled to sense a physiologic response to the delivery of pressure, and thereby to determine tissue perfusion pressures. Embodiments of the Foley type catheter include a pressure sensor having a pressure interface disposed at a distal end of the catheter, a pressure transducer at a proximal end of the catheter, and a fluid column disposed between the pressure interface and the pressure transducer. Embodiments of this type further include an expandable pressure-delivery balloon disposed on the catheter so as, upon expansion, to contact a wall of the bladder or the urethra, and a light source and a light sensor disposed proximate the tissue-compressing balloon. When an embodiment of catheter is appropriately or functionally inserted into the urinary tract with the distal end residing in the bladder, the pressure transducer can transduce pressure impinging on it from the pressure interface into a chronological pressure profile. The pressure profile has sufficient resolution to be processed into one or more distinct physiologic pressure profiles, including peritoneal pressure, respiratory rate, and cardiac rate. And when the expandable pressure balloon is expanded so as to blanche a tissue surrounding it (as detected by the light sensor), a light-based signal emanating from the light sensor may be processed to yield a perfusion pressure on a urinary bladder wall or a urethra.

The disclosed technology further relates to a system for sensing and processing physiologic data from the urinary tract of a patient, the physiologic data particularly including those gathered by high fidelity pressure sensing and transduction into signals suitable for processing; these embodiments will now be summarized. In some embodiments, the pressure-sensing Foley type system may further be enabled to sense and process temperature data and/or analyte data of clinical significance; these features and embodiments will be summarized further, below.

Thus, particular embodiments of the disclosed technology relate to a system for sensing pressure-based physiologic data from the urinary tract of a patient. Embodiments of the system include a Foley type catheter with a pressure sensor having a pressure interface disposed at a distal end of the catheter, a pressure transducer at a proximal end of the catheter, and a fluid column disposed between the pressure interface and the pressure transducer. When the catheter is appropriately or functionally inserted into the urinary tract and the distal end is residing in the bladder, the pressure transducer can transduce pressure impinging on it from the pressure interface into a chronological pressure profile. Embodiments of the system further include a data processing apparatus in communication with the pressure transducer so as to be able to acquire the physiological data. Embodiments of the data processing apparatus are configured to process the chronological pressure profile into one or more physiologic pressure profiles from the group including peritoneal pressure, respiratory rate, and cardiac rate.

In particular embodiments of the system, the pressure transducer is operable to sample pressure impinging on it at a rate of at least about 1 Hz. In embodiments such as these, the data processing apparatus may be configured to determine relative pulmonary tidal volume. In other particular embodiments of the system, the pressure transducer is operable to sample pressure impinging on it at a rate of at least about 5 Hz. In embodiments such as these, the data processing apparatus may be configured to determine any of cardiac output, relative cardiac output, or absolute cardiac stroke volume.

In particular embodiments of the system, the Foley type catheter may further include a temperature sensor to monitor body temperature. In embodiments such as these, the data processing apparatus may be further configured to acquire and process signals from temperature sensor.

In other embodiments of the system, the Foley type catheter may further include one or more analyte sensors. In embodiments such as these, the data processing apparatus is further configured to acquire and process signals from the one or more analyte sensors.

In some embodiments of the system, the data processing apparatus includes a stand-alone console. In some embodiments, the stand-alone console includes a bedside unit that is dedicated to monitoring a single patient. In some of these types of embodiments, the communication between the pressure transducer and the data processing apparatus is wireless.

In some embodiments of the system, the data processing apparatus includes a networked computer. In some of these types of embodiments, the networked computer is able to track data from a plurality of patients.

In particular embodiments of the system, the data processing apparatus may include both a stand-alone console and a networked computer. In some of these types of embodiments of this type, the stand-alone console and the networked computer are in communication with each other. In particular embodiments, the in communication between the stand-alone console and the networked computer is wireless.

In some embodiments of the system, the data processing apparatus may include a memory into which a normal range of values for the physiologic data may be entered, and the data processing apparatus may be configured to initiate an alarm when physiologic data of the patient are outside such range of normal values.

In some embodiments of the system, the data processing apparatus may include a memory configured to receive patient-specific clinical data from a source external to the Foley type catheter, and the data processing apparatus may be configured to integrate such external data and the Foley type catheter-derived physiologic data.

Some embodiments of the system may include a controller in communication with the data processing apparatus. In such embodiments, the controller may be configured to tune a level of pressure being applied through the fluid column against the proximal side of the pressure interface. Aspects of tuning the pressure level being applied distally against the pressure interface are expanded on below, in the context of summarizing methods provided by the disclosure. Further, in embodiments of the catheter that include a pressure delivery balloon that may be used in a method to measure tissue perfusion pressure, the controller may be configured to controllably expand such pressure delivery balloon.

In some embodiments of the system, the physiologic data from the pressure sensor may be used to track clinical parameters relevant to monitoring intraabdominal hypertension (IAH) or abdominal compartment syndrome (ACS). In other embodiments of the system, the physiologic data from the pressure sensor may be used to track clinical parameters relevant to monitoring any of cardiac status, respiratory status, the onset and progression of hemorrhage or shock, patient bodily movement, or intestinal peristalsis.

As noted above, some embodiments of the disclosed technology relate to a system for sensing pressure-based and temperature-based physiologic data from the urinary tract of a patient, such system including a Foley type catheter with a pressure sensor and a temperature sensor. Embodiments of the pressure sensor have a pressure interface disposed at a distal end of the catheter, a pressure transducer at a proximal end of the catheter, and a fluid column disposed between the pressure interface and the pressure transducer. When the catheter is appropriately or functionally inserted into the urinary tract and the distal end is residing in the bladder, the pressure transducer transduces pressure impinging on it from the fluid column into physiological data comprising a chronological pressure profile. Embodiments of the system further include a data processing apparatus in communication with the pressure transducer so as to be able to acquire the physiological data. Embodiments of the data processing apparatus are configured to process the chronological pressure profile into one or more physiologic pressure profiles from the group including peritoneal pressure, respiratory rate, and cardiac rate. Embodiments of the data processing apparatus are further configured to acquire and process signals from the temperature sensor, such signals reporting the core body temperature of the patient.

Some embodiments of the disclosed technology relate to a system for sensing pressure-based and analyte-based physiologic data from the urinary tract of a patient, such system including a Foley type catheter with a pressure sensor and one or more analyte sensors. Embodiments of the pressure sensor have a pressure interface disposed at a distal end of the catheter, a pressure transducer at a proximal end of the catheter, and a fluid column disposed between the pressure interface and the pressure transducer. When the catheter is appropriately or functionally inserted into the urinary tract and the distal end is residing in the bladder, the pressure transducer transduces pressure impinging on it from the fluid column into physiological data comprising a chronological pressure profile. Embodiments of the system further include a data processing apparatus in communication with the pressure transducer so as to be able to acquire the physiological data. Embodiments of the data processing apparatus are configured to process the chronological pressure profile into one or more physiologic pressure profiles from the group including peritoneal pressure, respiratory rate, and cardiac rate. Embodiments of the data processing apparatus are further configured to acquire and process analyte signals from the one or more analyte sensors, such signals reporting the level of one or more analytes within the urinary tract.

As noted above, some embodiments of the disclosed technology relate to a system for sensing pressure-based, temperature-based, and analyte-based physiologic data from the urinary tract of a patient, such system including a Foley type catheter with a pressure sensor, a temperature sensor, and one or more analyte sensors. Embodiments of the pressure sensor have a pressure interface disposed at a distal end of the catheter, a pressure transducer at a proximal end of the catheter, and a fluid column disposed between the pressure interface and the pressure transducer. When the catheter is appropriately or functionally inserted into the urinary tract and the distal end is residing in the bladder, the pressure transducer transduces pressure impinging on it from the fluid column into physiological data comprising a chronological pressure profile. Embodiments of the system further include a data processing apparatus in communication with the pressure transducer so as to be able to acquire the physiological data. Embodiments of the data processing apparatus are configured to process the chronological pressure profile into one or more physiologic pressure profiles from the group including peritoneal pressure, respiratory rate, and cardiac rate. Embodiments of the data processing apparatus are further configured to acquire and process signals from the temperature sensor, such signals reporting the core body temperature of the patient. Embodiments of the data processing apparatus are further configured to acquire and process analyte signals from the one or more analyte sensors, such signals reporting the level of one or more analytes within the urinary tract.

In some embodiments of the system, the physiologic data from the any one or more of the sensors (pressure sensor, temperature sensor, and/or analyte sensor) may be used to track clinical parameters particularly relevant to monitoring clinical conditions brought about by metabolic diseases or diseases with pathophysiologic metabolic symptoms. For example, embodiments of the system may be used to monitor clinical parameters relevant to kidney function or diabetes. In other embodiments of the method, the physiologic data from the sensors, the pressure sensor in particular, may be used to monitor body movement.

Some embodiments of the system include a fluid-collecting receptacle to collect urine drained from the bladder, and the receptacle may include a fluid volume measuring system. In some of such embodiments, the fluid volume measuring system is configured to deliver data from which a urine output rate may be determined. Embodiments of the fluid volume measuring systems may include any of a weight-sensitive system, a fluid height sensing system, a mechanical mechanism, or an optically-sensitive system.

Some embodiments of the fluid-collecting receptacle may include a chemical analyte measuring system to identify and/or quantitate analytes such as those summarized for the Foley type catheter itself. More specifically, as example, analyte sensors may be sensitive to any one or more analytes selected from a group consisting of bacteria, blood, hemoglobin, leukocyte esterase, glucose, and particulate matter.

Some embodiments of the fluid-collecting receptacle may include an RFID chip for identification of the receptacle in communications with a data processing apparatus, or for conveying sensed data to the data processing apparatus.

Some embodiments of the system may include a docking station to accommodate the collecting receptacle, wherein the docking station and the collecting receptacle are in electrical communication with each other. Communication between the docking station and the collecting receptacle may occur by way of a data transmission line connecting the docking station to the console, or it may occur by way of a wireless communication system.

Some embodiments of the system may include a fluid infusion apparatus, with the data processing apparatus being configured to control the activity of the fluid infusion apparatus in response to physiologic data processed by the data processing apparatus.

Some embodiments of the disclosed technology relate to a method for monitoring physiologic data from the urinary tract of a patient. These physiologic data particularly include pressure-based data, but may further include temperature-based data and analyte-based data. In still further embodiments, delivery of pressure in combination with light-based data to yield tissue perfusion pressure values.

Embodiments of the method include providing a physiologic data monitoring system that includes a Foley type catheter and a data processing apparatus. Embodiments of the Foley type catheter have a pressure sensor, the pressure sensor having a pressure interface disposed at a distal end of the catheter, a pressure transducer at a proximal end of the catheter, and a fluid column disposed between the pressure interface and the pressure transducer, the pressure transducer being able to transduce pressure impinging on it from the fluid column into physiological data comprising a chronological pressure profile. The method may further include inserting the Foley type catheter in the urinary tract such that the pressure interface is residing within the patient's bladder; transferring pressure sensed in the bladder into a transducible chronological pressure profile; and processing the chronological pressure profile into one or more physiologic pressure profiles selected from the group consisting of peritoneal pressure, respiratory rate, and cardiac rate.

Some embodiments of the method include tuning or priming a level of pressure being applied from a proximal side of the pressure interface of a Foley type catheter toward equivalence with a baseline physiologic pressure being applied to a distal side of the pressure interface. Tuning pressure refers generally to either increasing or decreasing pressure applied to the proximal side of the pressure interface. Proximal, in this context, refers to the side of the pressure interface facing outward from the body (within the communicating fluid column), and toward the main body of the catheter or an operator handling the catheter. In one aspect, tuning the pressure level may refer to priming the fluid column from the proximal end of the column, directing pressure toward the distal end of the column. In another aspect, tuning the pressure level may refer to releasing or bleeding pressure from the proximal end of the column, as may be appropriate, for example, if pressure in the column overshoots a desired pressure level, or if pressure from within the bladder were to decrease. Embodiments of the method may further include repeating the tuning step, as needed, to maintain equivalence between the level of pressure being applied from the proximal side of the pressure interface and the baseline physiologic pressure being applied to a distal side of the pressure interface.

Embodiments of the tuning step of the method may include monitoring a physiologic pressure profile, and adjusting the pressure being applied from a proximal side of the pressure interface to a level such that a quality of a physiologic pressure profile being processed by the system is optimized. By way of example, the amplitude of pressure waves associated with the respiratory rate may be monitored. A high amplitude pressure profile may be considered optimal in that it is generally associated with conditions of equivalence between baseline pressure on either side of the pressure interface. In another aspect, a high amplitude pressure profile may be considered optimal because, other factors being equal, a high amplitude signal permits a higher level of resolution of real differences that may appear in signal level. In some embodiments, the monitoring step may be performed automatically by the data processor, and the adjusting step may be performed by an automatic controller in communication with the data processor.

The necessity to prime the catheter is driven, at least in part, by leakage of gas from the fluid column. It has been observed, for example, that a Foley type catheter, per embodiments of the disclosed technology, that comprises a thin silicone membrane (e.g., a membrane with a thickness of 0.003 inch) leak about 2 cc of air per hour when under 15 mm Hg of pressure.

Some embodiments of the method may include applying pressure to the proximal side of the pressure interface by delivering gas under pressure to a space proximal to the pressure interface. Delivering gas to the space proximal the pressure interface may be considered priming the space or tuning the space so as to equilibrate or substantially equilibrate pressure on either side of the pressure interface. The source of the gas, per embodiments of the technology, is typically a compressed gas cylinder. Any suitable biologically compatible gas may be used, including, by way of example, air or carbon dioxide.

In some embodiments of the method, appropriate for those in which the pressure interface includes a balloon formed from an inelastic membrane, the method further includes priming the fluid column from the proximal end of the catheter to maintain the balloon at a size that places no substantial strain on the inelastic membrane.

In some embodiments of the method, appropriate for those in which the pressure interface includes a balloon formed from an inelastic membrane having a total surface area, the method further include inflating the balloon to a level such that the total surface area of the membrane is substantially taut.

Some embodiments of the method include sampling the pressure profile impinging on the transducer at a frequency of at least 1 Hz, the method further comprising quantifying respiratory excursions relative to a baseline magnitude of excursions proximate the time of catheter insertion. These embodiments may particularly include monitoring the relative amplitude of respiratory pressure wave excursions, and relating such relative amplitude to relative respiratory tidal volumes.

Some embodiments of the method include sampling the pressure profile impinging on the transducer at a frequency of at least 5 Hz, the method further including quantifying peaks on the respiratory pressure wave that are associated with the cardiac rate. In particular embodiments of this type, against a background of a substantially stable peritoneal pressure, the method may further include determining any of cardiac output, relative cardiac output, respiratory tidal volume, or absolute cardiac stroke volume.

In some embodiments of the method, the one or more physiologic pressure profiles yielded by processing the chronological pressure profile may provide for monitoring of body movement. Monitoring body movement may be of particular benefit for bed-ridden patients, for example, who have a decubitis ulcer, or are at risk of developing such an ulcer when a portion of the body, such as a bony prominence, rests too long in a pressured position without movement that would relieve such pressure. Accordingly, monitoring body movement may include notifying a health care provider of the level of movement of a patient who is at risk of developing a decubitis ulcer, or at risk of exacerbating an existing decubitis ulcer. In addition, monitoring of patient activity may also affirmatively report the presence of movement. In this case, a patient that is a fall risk can be monitored for activity that may indicate an attempt to rise from their bed. This may signal an alert and prevent their mobility without assistance.

In some embodiments of the method, wherein the Foley type catheter has an expandable pressure delivery balloon, a light source and a light sensor proximate the expandable pressure balloon (the light sensor configured to capture light from the light source) the method may further include inflating the pressure delivery balloon to a desired pressure, and monitoring the pressure within the expandable balloon to determine the pressure level required to blanche the tissue, said blanching pressure being reflective of a tissue perfusion pressure.

In some embodiments of the method, wherein the Foley type catheter has a temperature sensor, the method may further include monitoring the body temperature of the patient. In some embodiments of the method, wherein the Foley type catheter further comprises an analyte sensor, the method further may further include monitoring a level of the analyte within the urine of the patient.

BRIEF DESCRIPTION OF THE DRAWINGS

FIG. 6A schematically arranges the sensing Foley catheter into a proximal section that remains external to the body when in use, a portion that resides in the urethra, and a portion that resides in the bladder, when placed into a human subject.

FIG. 6B shows a detailed view of the proximal portion of the catheter.

FIG. 6C shows a cross sectional view of the central length of the catheter.

FIG. 6D shows a detailed view of the distal portion of the catheter that resides in the bladder.

FIG. 7B shows a detailed portion of the respiratory profile of FIG. 7A, a portion of the period of normal respiration.

FIG. 8 shows an example of cardiac rate and relative cardiac output sensing data from a human subject, as provided by an embodiment of the sensing Foley catheter system, and an EKG trace as measured simultaneously and independently.

FIG. 12 shows intraabdominal pressure, respiratory wave pressure, and cardiac pressure schematically arrayed as a two dimensional plot of pressure (mm Hg on a logarithmic scale vs. frequency (Hz).

FIG. 13 provides a flow diagram of an embodiment of the method.

DETAILED DESCRIPTION OF THE DISCLOSURE

Figure 1:
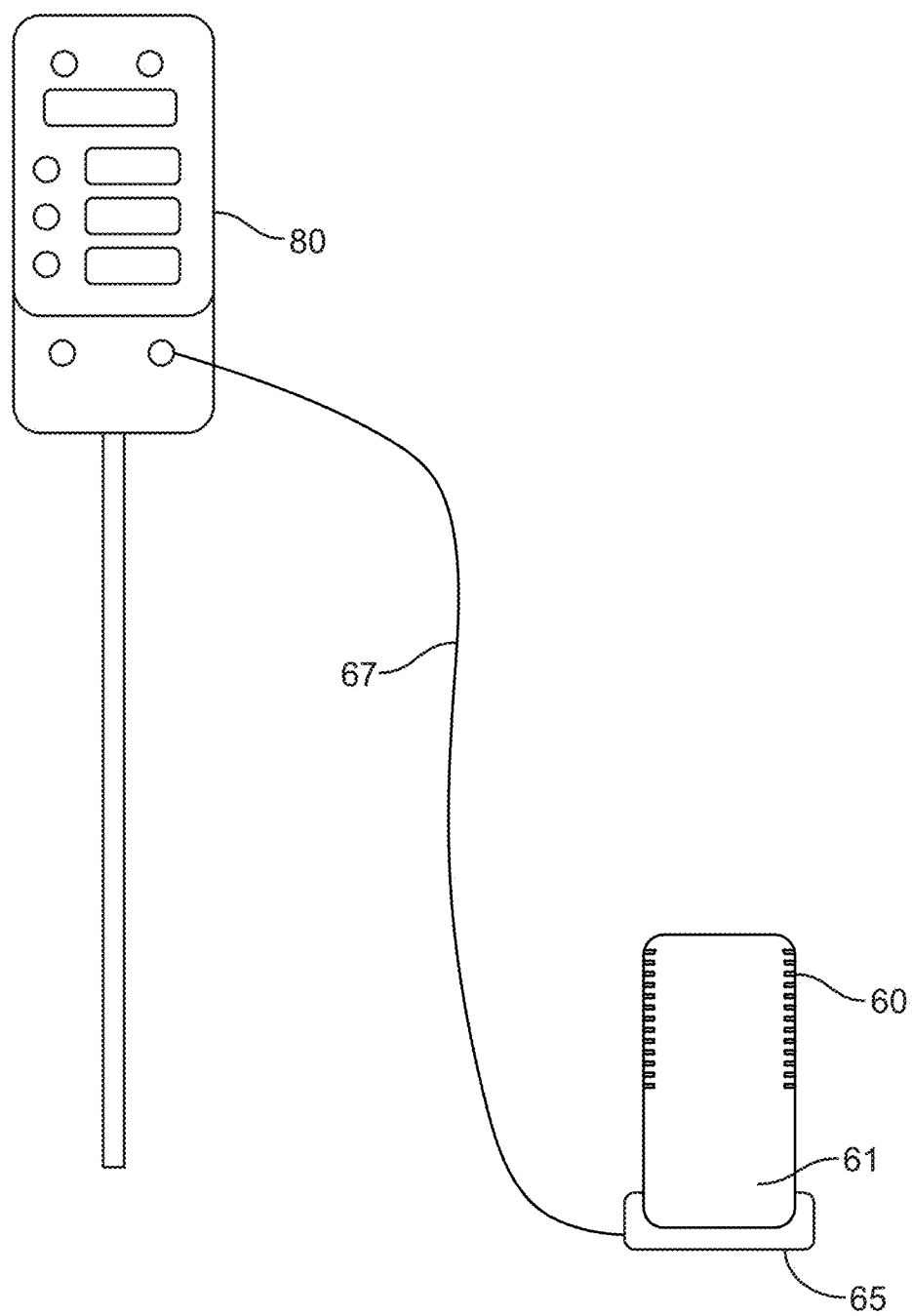
FIG. 1 shows a data console in communication with a urine-collecting receptacle docking station, per an embodiment of the sensing Foley catheter system.

FIGS. 1-4 show various elements of the disclosed technology, including a urine receptacle 60 (holding a urine output 61), a docking station 65 to hold the receptacle, an electrical connection 67 that allows communication between the docking station and a data collection and processing apparatus in the form a bedside console 80. Embodiments of the urine collecting receptacle 60 may include level or volume sensors 62, as well as other analyte sensors. Receptacle 60 may also include an RFID element that provides a unique identifier to a remote RFID reader 68. In some embodiments, an extender tube 63 may be utilized to convey urine from the catheter to the urine-collecting receptacle.

FIG. 1 shows a data receiving and processing apparatus in the form of a bedside console 80 in communication with a receptacle docking station 65 that accommodates a urine collecting receptacle 60, shown as holding a urine output 61, per an embodiment of the sensing Foley catheter system. The communication path between the docking station and the console may include a wired connection 67, as shown, or it may be a wireless connection. The bedside console may record and display output/input data. Physiologic data from sensors associated with a sensing Foley catheter may be held in a memory, displayed, printed, or directly transmitted to a centralized data collection server.

In some embodiments, the bedside console or controller is portable and able to travel with the patient. Embodiments of console may be attachable to a patient's bed or an IV pole, or a wall mount; it typically has its own display, and is able to provide critical alerts. Some embodiments of console may be adapted to be able to operate on a battery backup for 4 or more hours, as for example when wall power is unavailable or has been lost. This portability feature of console is advantageous in situations where patients are typically not being electronically monitored, such as when a patient is in transit from his or her bed to another location. Embodiments of console may also be configured to communicate to a base station with alerts and centralized reporting and data collection. A controller or base station may also generate mobile alerts that may be sent to nurses or healthcare provider. Signal analysis and/or predictive algorithms may also be used to provide useful clinical data from sensors.

Figure 2:
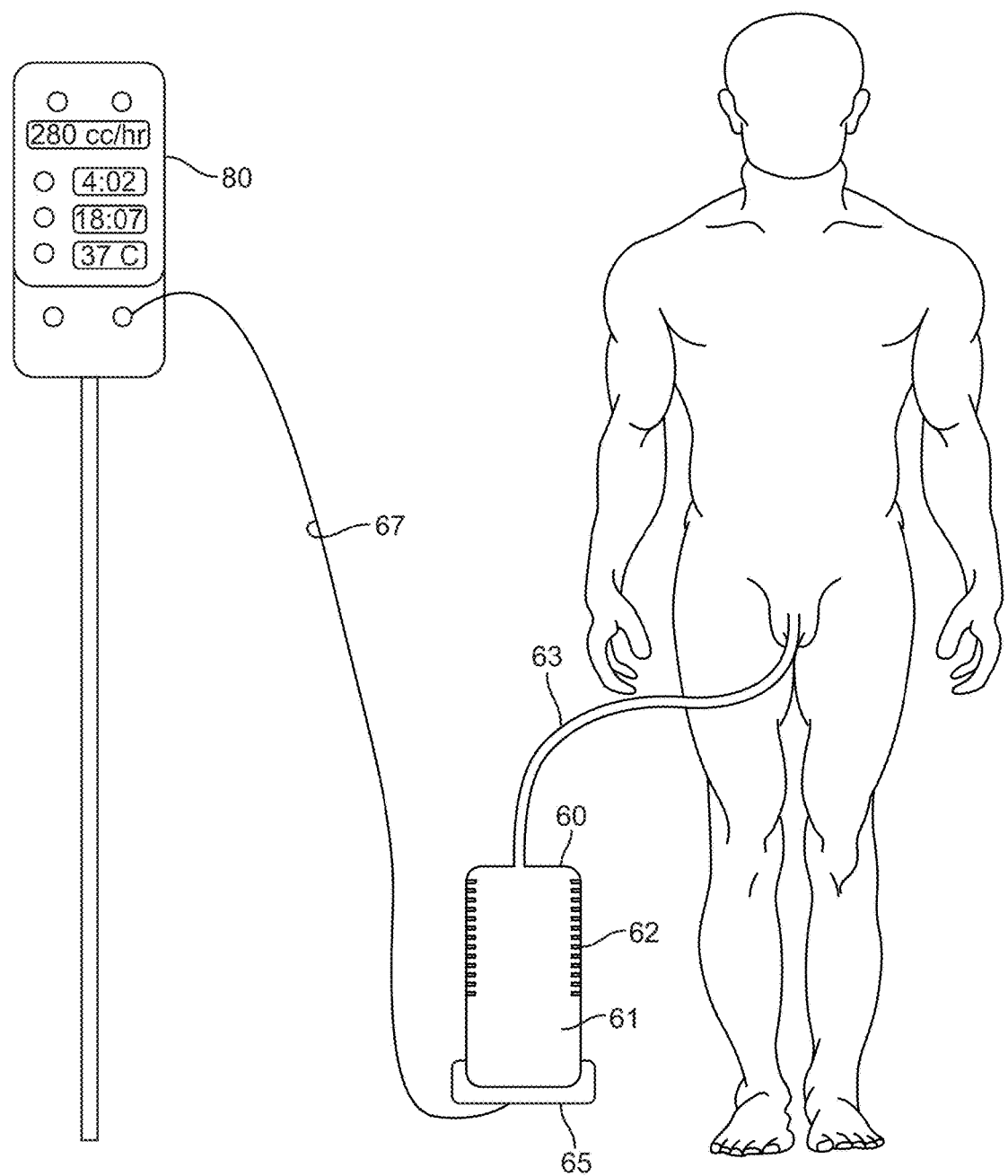
FIG. 2 shows an embodiment of the sensing Foley catheter system set up to measure urine output from a human subject.

FIG. 2 shows elements of an embodiment of the sensing Foley catheter system configured to measure urine output from a human subject. In some embodiments, the bedside console 80 or an RFID reader (see FIG. 5) is enabled to trigger an alert if urine output is above or below a preset normal or desired range for urine output over a set period of time. Some embodiments of the system may also have an intravenous infusion capability (see FIG. 3) to provide use sensed data to regulate delivery of fluids or medicinal agents such as a diuretic drug, by way of an automated system based on the urine output feedback. Embodiments of the system may include a docking station for the urine collecting receptacle, the docking station being configured for data transmission to a data receiving and processing apparatus such as a bedside console or a networked central computer. In some embodiments, the docking station delivers data regarding the volume of urine in the urine receptacle, as well as data that are informative regarding electrical parameters of the urine, such as conductivity, resistance, or impedance. Sensors may also detect and monitor bacteria, hemoglobin, or other substances of clinical significance in urine.

Figure 3:
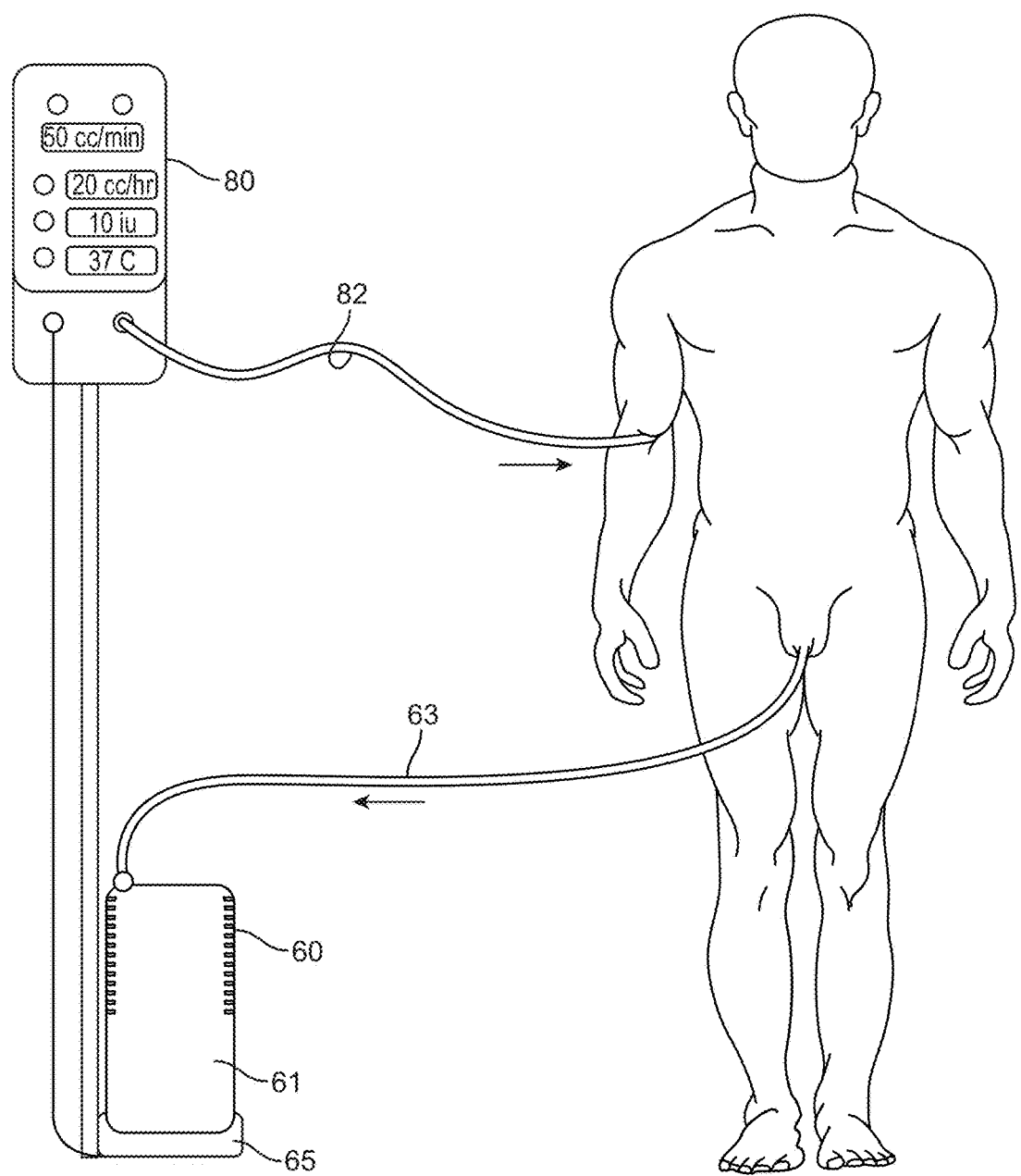
FIG. 3 shows an embodiment of the sensing Foley catheter system set up as an automated infusion therapy system for a human subject.

FIG. 3 shows an embodiment of the sensing Foley catheter system configured as an automated infusion therapy system for a human subject. A bedside console 80 may integrate patient data, such as fluids received or urine output recorded, and then automate therapeutic infusion in response to these data. For example, delivery of fluids or drug solutions such as a physiological saline solution may be initiated or regulated through an infusion line 82 if the patient is dehydrated, or a diuretic may be infused if the patient is fluid overloaded. In some embodiments, the console may trigger a local alert (e.g., audible beeping), or trigger a centralized alert (e.g., a system alarm) if urine output drops too low. The console may also integrate a hydrating or medicinal fluid infusion capability, such as an IV infusion pump, and may adjust infusion rates based on these data or based on data acquired from other sensors automatically. The console may communicate wirelessly, as well, to these and other sensors within the body.

Figure 4:
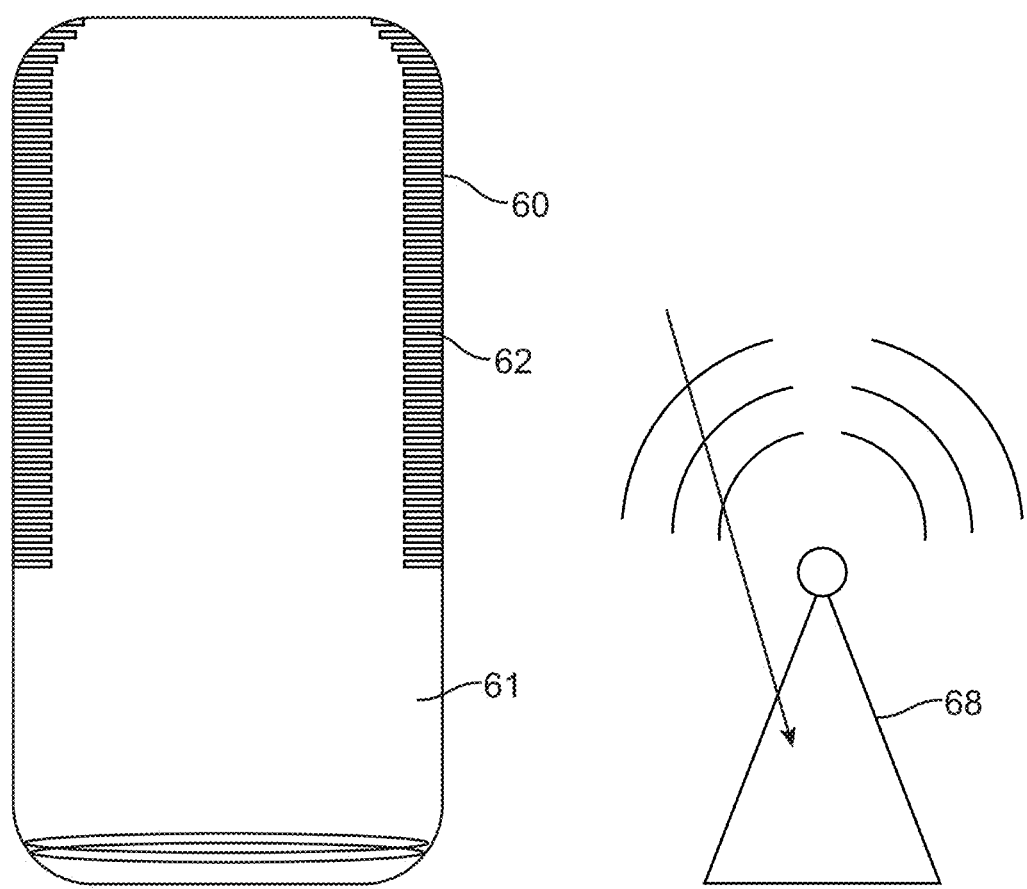
FIG. 4 shows a volume-sensing urine collecting receptacle that includes an RFID chip, the receptacle accommodated within a receptacle docking station, per an embodiment of the sensing Foley catheter system.

FIG. 4 shows a volume-sensing urine receptacle 60 accommodated within a receptacle docking station 65, per an embodiment of the sensing Foley catheter system. Embodiments of the receptacle may detect urine output based on the levels at which sensors 62 are triggered. For example, the receptacle may include electrical contacts arranged as liquid height-marks, and when an electrical path is made between two contacts and all contacts below, the level can be reported at that level. Embodiments of the receptacle may include electrical, optical, chemical or mechanical sensors. Embodiments of the receptacle may include also contain diffuse or discrete sensing areas that detect analytes of interest, e.g., hemoglobin, protein, glucose, bacteria, blood, leukocyte esterase. Sensing or data reporting of sensed data may be of either an intermittent or a continuous nature.

Embodiments of the receptacle may include a capability to report sensing data to the bedside console, locally (e.g., by beeping) or centrally via piping data to a central information collection area. For example, an alert may be triggered if urine output drops below 30 cc/hr. in post-operative setting or below any otherwise predetermined threshold. Embodiments of the receptacle may connect to a docking station through electrical contacts; data communication among embodiments of the receptacle, docking station, and a console or central computer may also be wireless. If a docking station is used, it may detect urine output based on weight or pressure of the receptacle that is applied to base.

Embodiments of the urine collecting receptacle may include disposable or durable optical, electrical or chemical sensors capable of sensing and measuring urine content of analytes such as glucose, electrolytes, bacteria, hemoglobin, or blood. Embodiments of the receptacle may include an interface with specifically designed area of the urine receptacle to allow for this measurement, such as an optically clear window for optical measurement of blood. Embodiments of the receptacle docking station may also grasp or accommodate the urine receptacle in any manner so long as it secures the receptacle. The docking station or the receptacle may include an inductive antenna or RFID capabilities to allow for wireless querying and reporting of the level of urine or other fluid collection.

The embodiment of FIG. 4 also shows a volume-sensing urine receptacle 60 that includes an RFID chip, per an embodiment of the sensing Foley catheter system. This embodiment may contain RFID circuitry to collect and transmit data directly from within the receptacle to a remote RFID reader 68. When queried by the RFID reader, the receptacle may detect impedance, resistance, capacitance or any other electrical or non-electrical property to measure the urine level and report this back to the reader. The reader may then trigger alert if urine output is out of a normal or desirable range. The RFID chip may be capable of detecting changes in optical, chemical, electrical, acoustic or mechanical properties, as well. RFID chips may be active or passive, and may contain an antenna to transmit a receptacle-identifying signal to the reader, and allow multiple receptacles to be queried simultaneously. An active RFID chip may incorporate a small battery (to extend its range). A passive RFID chip may be powered by the transmission from the RFID reader. The RFID reader may query a device from a distance to wirelessly check the urine output level or it may be centralized to query all receptacles within a unit, floor or hospital and issue an alert if urine output is out of a normal or desirable range. The RFID reader record urine output, as well, and functionally replace the individual unit console shown in FIGS. 1-3. The RFID reader may also report data from other sensors within the system, including bladder temperature or presence of analytes (as detailed elsewhere) in the urine.

FIGS. 5A-6D show embodiments of a sensing Foley catheter 10 and various of its features. A catheter may be understood to have various sections according to their disposition when the catheter is inserted into a human subject, such as a proximal portion 14 that remains external to the subject, a central or urethra-residing portion 13, and a distal or urinary bladder-residing portion 12.

Various internal lumens traverse the length of the catheter, such as an air or fluid 24 that communicates with a bladder retention balloon 36. A urine drainage lumen 23 has a distal opening 41 that resides in the bladder portion 12 of the catheter, and has an opening at the proximal end 14 of the catheter. As seen in FIGS. 2 and 3, the urine drainage lumen may be connected to an extender tube 63 that conveys the urine to a collecting receptacle. In some embodiments, the drainage lumen and distal opening in the bladder may also serve as in infusion conduit (see FIG. 3) by which medicinal agents may be infused, or through which heating or cooling fluid may be infused. Analyte sensors or temperature sensors 50 may be disposed on the catheter, either on the urethral portion 10 or the bladder-residing portion 12 of the catheter. Electrical or optical fiber leads may be disposed in a lumen 25 that allows communication of sensing signals between distally disposed sensors and the proximal portion of the catheter, and then further communication to a data processing apparatus.

An inflatable pressure-sensing balloon 38 (FIGS. 6A, 7A, and 7B) or a pressure sensing membrane 39 (FIG. 5B) arranged across an opening may be positioned on the distal end 12 of the catheter, residing in the bladder. Embodiments of a pressure-sensing balloon or pressure sensing membrane may be understood as comprising a pressure interface having a distal-facing surface exposed to pressure from within the bladder, and a proximal-facing surface exposed to a proximal fluid column. Embodiments of the fluid column (filled with either liquid or gas) may comprise a dedicated lumen, or such column may share a lumen that also serves as a sensing conduit such as lumen 25.

Figure 5A:
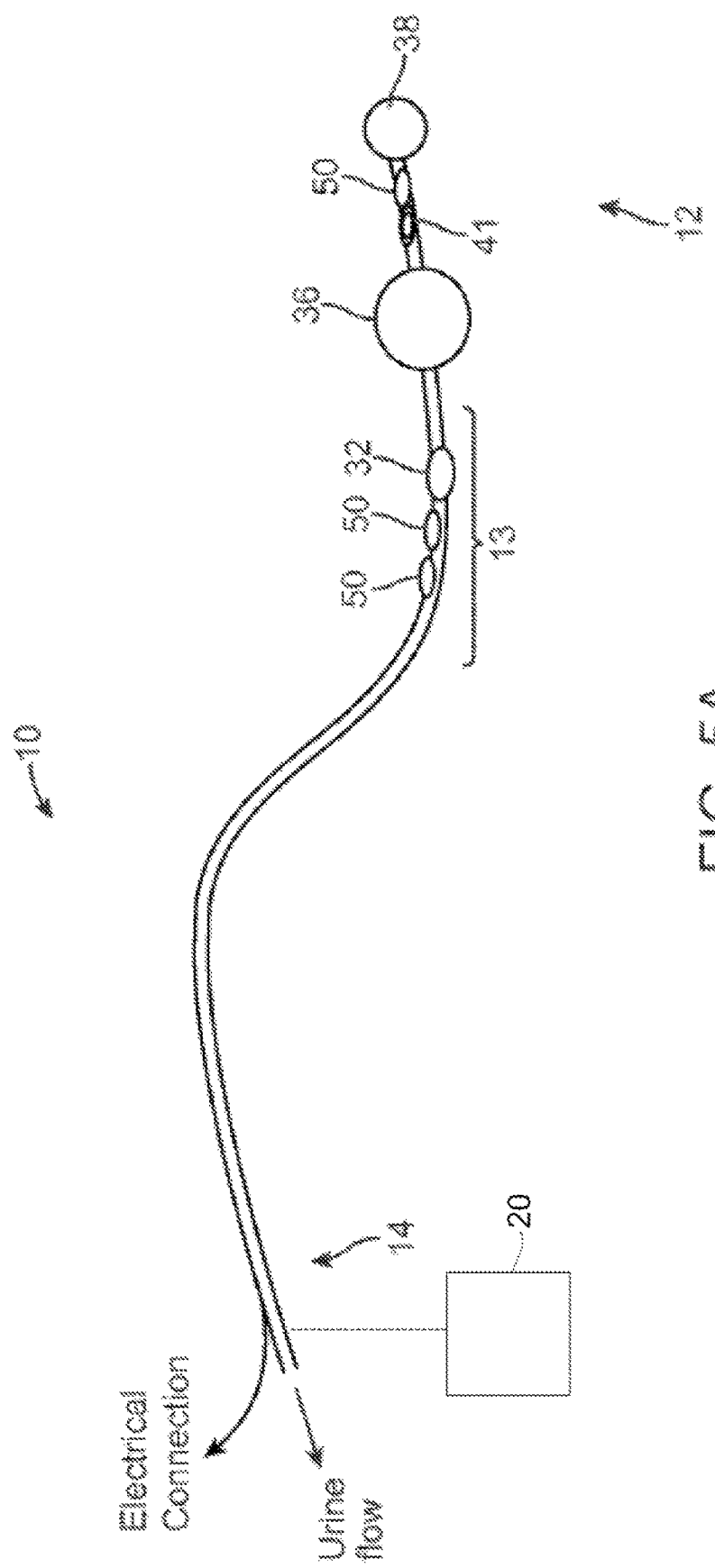
FIG. 5A shows a sensing Foley catheter with a pressure interface in the form of an inflatable balloon, per an embodiment of the sensing Foley catheter system.

FIG. 5A shows a sensing Foley catheter that includes a pressure interface in the form of pressure-sensing balloon, per an embodiment of the presently disclosed system. Pressure-based physiologic parameters that this catheter embodiment can sense may include, by way of example, peritoneal pressure, respiratory rate, and cardiac rate, relative pulmonary tidal volume profile, cardiac output, relative cardiac output, and absolute cardiac stroke volume. Some embodiments of the Foley type catheter may be further equipped with any of a temperature sensor, one or more analyte sensors, electrodes, and paired light sources and sensors. Embodiments thus further equipped are capable of delivering other forms of physiologic data, as for example, blood pressure, oxygen saturation, pulse oximetry, EKG, and capillary fill pressure. A pressure transducer 20 is further shown connected at the proximal end of the catheter external to the body.

Figure 5B:
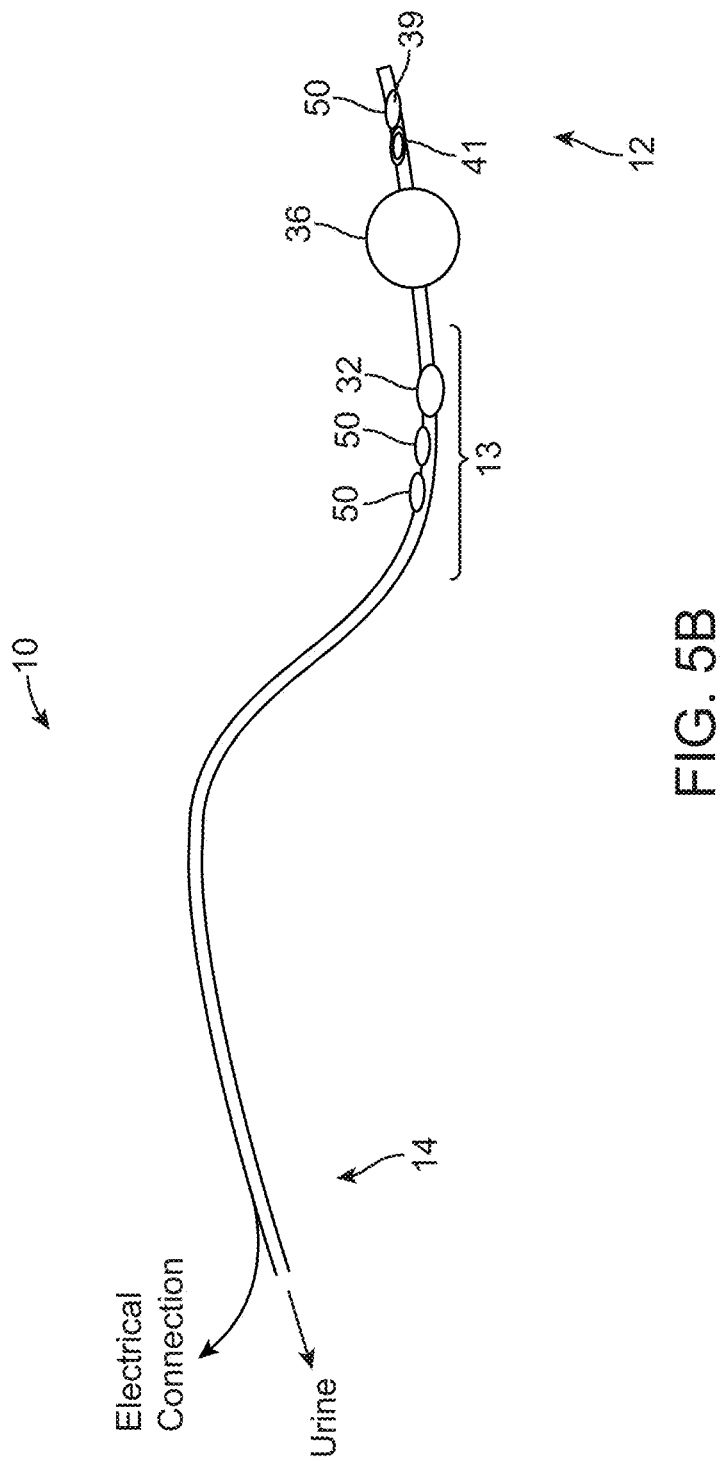
FIG. 5B shows a sensing Foley catheter a pressure interface in the form of a membrane arranged across a luminal opening, per an embodiment of the sensing Foley catheter system.
Figure 6:
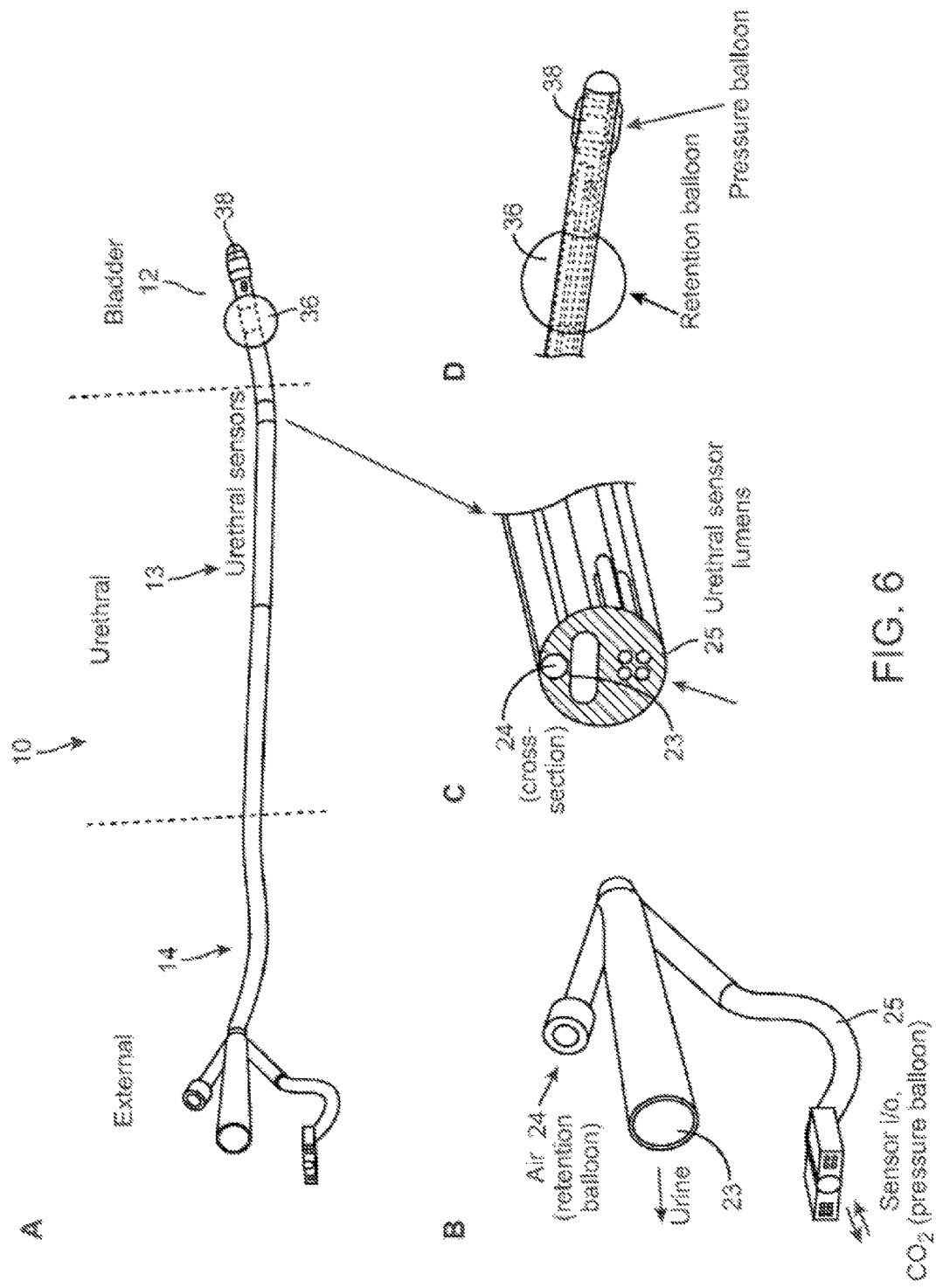
FIGS. 6A-6D show various views and details of a sensing Foley catheter, per an embodiment of the sensing Foley catheter system.

FIG. 5B shows a sensing Foley catheter with a lumen (the third lumen, for example) used as a pressure sensing lumen; this embodiment does not include a dedicated pressure-sensing balloon as does the embodiment of FIG. 5A, but instead has a pressure interface in the form of a membrane arranged over a distal opening of the pressure sensing lumen. In this embodiment, the sensing Foley catheter is able to detect and report pressure-based physiologic data as included in the embodiment described above. In this present embodiment, a slow infusion of fluid into the bladder may be accomplished through the third lumen of a standard 3-way Foley catheter, and pressure may be sensed using a pressure sensor in line with this third lumen. In this embodiment, all methods associated with processing and responding to pressure-based physiologic data, as described for embodiments with a pressure-sensing balloon, are enabled.

FIGS. 6A-6D show various views and details of a sensing Foley catheter, per an embodiment of the sensing Foley catheter system. FIG. 6A schematically arranges the sensing Foley catheter into a proximal section 14 that remains external to the body when in use, a portion 13 that resides in the urethra, and a distal portion 12 that resides in the bladder, when placed into a human subject. FIG. 6B shows a detailed view of the proximal portion of the catheter, focusing on luminal openings 23, 24, and 25, which are configured to make more proximal connections. FIG. 6C shows a cross sectional view of the central length of the catheter, and an example of how lumens 23, 24, and 25 may be arranged. FIG. 6D shows a detailed view of the distal portion of the catheter that resides in the bladder, with a particular focus on a retention balloon 36 and a pressure-sensing balloon 38.

Pulse oximetry elements allow for a determination of blood oxygen concentration or saturation, and may be disposed anywhere along the urethral length of the catheter. In some embodiments, the sensor or sensors are disposed within the tubing of the device to ensure approximation to the urethral mucosa. With this technology, a healthcare provider can decompress the bladder with a urinary catheter and obtain pulse oximetry data in a repeatable and accurate manner. The power source for pulse oximetry may be incorporated within the urinary collecting receptacle or within the catheter itself. In some embodiments, the pulse oximeter is reusable and the catheter interface is disposable; in this arrangement the pulse oximeter is reversibly attached to the disposable catheter and removed when oxygen measurements are no longer desired. Embodiments of the sensing Foley catheter may include an optically transparent, or sufficiently transparent, channel for the oximetry signal, such as a fiber-optic cable, transparent window, and an interface for the reusable oximeter. This method and device for urethral pulse oximetry may be used in conjunction with any of the other embodiments detailed herein or may be a stand-alone device.

Embodiments of the sensing Foley catheter may be able to sense any one or more of a plurality of clinically relevant parameters, such as included in the following examples: urine pH, urine oxygen content, urine nitrate content, respiratory rate, heart rate, perfusion pressure of the bladder wall or the urethral wall, temperature inside the bladder or the urethra, electro-cardiography via sensors on the bladder wall or the urethra, respiratory volume, respiratory pressure, peritoneal pressure, urine glucose, blood glucose via urethral mucosa and/or bladder mucosa, urine proteins, urine hemoglobin, blood pressure. In some embodiments, the catheter can sense multiple parameters, but some embodiments may be limited to as few as a single parameter for focused applications (for example, respiratory rate in a patient in respiratory distress). The respiratory rate, relative tidal volume, peritoneal pressure, heart rate and/or relative cardiac output may be measured simultaneously, as well, by connecting a balloon with a flaccid wall or semi-tense wall to an external pressure sensor via a lumen that may be filled with liquid and/or gas.

These parameters may be measured, alone or in concert with other parameters, through the use of pressure measurement modalities other than the external pressure sensor. These may include: a deflecting membrane inside of the catheter, MEMs technology, a catheter-based sensor and/or other embodiments.

Relative cardiac output and relative tidal volume may also be calculated, based on the deflection of the pressure sensor and/or other force gauge. If sampled with sufficient frequency (e.g., 1 Hz or greater), respiratory excursions can be quantified in a relative manner to the amplitude of the excursions at the time of catheter placement. Larger excursions generally relate to heavier breathing, or in the setting of an upward drift in the baseline, a higher peritoneal pressure. The small peaks on the oscillating respiratory wave, caused by the pumping heart, may be tracked as well by using faster sampling rates (e.g., 5 Hz or greater), and the amplitude of this wave may be used, in the setting of a relatively constant peritoneal pressure, to determine the relative cardiac output, in the setting of a known, stable peritoneal pressure, absolute stroke volume and/or cardiac output.

The disclosed technology captures a high-resolution chronological profile (pressure as a function of time) of peritoneal pressure that can be transduced and processed into distinct pressure profiles assignable to particular physiologic sources, including peritoneal pressure, respiratory rate, and cardiac rate. By tracking the pressure profile at a sufficiently rapid sampling rate, as provided by the technology, the pressure profile can be further resolved into relative pulmonary tidal volume, cardiac output, relative cardiac output, and absolute cardiac stroke volume.

Accordingly, aspects of the disclosed technology relate to fidelity and resolution of a pressure signal generated in response to changes in pressure within the bladder, such changes being reflective of a pressure profile within the peritoneal cavity, such pressure profile including cumulative input from the aforementioned physiologic sources. Aspects of the technology further relate to fidelity and resolution of the transduction of the pressure signal into a highly resolvable electrical signal. Aspects of the technology relate still further to processing the totality of the electrical signal profile, a surrogate for the pressure profile within the peritoneal cavity, into component profiles that can be assigned to the physiologic sources.

The sensitivity of an inflated balloon as a pressure sensor is a function, in part, of the pressure differential across the balloon membrane as a baseline condition. The balloon has the greatest sensitivity to pressure when the baseline pressure differential is near zero. As the baseline pressure differential increases, the sensitivity of the pressure-sensing balloon degrades. Accordingly, the disclosed technology provides an automatic priming method that maintains the balloon in an inflated state, but with a minimal pressure differential.

Embodiments of the technology include a pressure interface as may be represented by a balloon having either a compliant membrane or a non-compliant membrane. In general, considerations related to optimizing the pressure around the pressure interface of the device are informed by Boyle's ideal gas law, the relationship between stress and strain as described by Hooke, and by application of Young's modulus. The conditions for optimal sensitivity of a compliant balloon and a non-compliant balloon are slightly different, although, in general, the sensitivity of each is best served by P1 and P2 being approximately equal. A non-compliant balloon maximum sensitivity is achieved when P1 is only slightly above P2. For a compliant balloon, the maximum sensitivity is achieved when P1 is slightly above P2 at the low end of the (linear) elastic region of the spring constant of the compliant balloon material.

To effectively capture physiologic pressure profiles, the profiles need to be sampled at a rate that is sufficient to resolve the inherent frequency of changes in the profile. This consideration is informed by the Nyquist-Shannon sampling theorem, which states that a sampling frequency of at least 2B samples/second is required to resolve an event that runs at a frequency of B cycles/second. As applied to a physiologic pressure cycle, for example, a cardiac rate of 70 beats/minute requires a sampling rate of at least 140 samples/minute to effectively capture the cycle. This relationship underlies aspects of the disclosed technology that specify the sampling rate particularly required to capture physiologic pressure cycles such as relative pulmonary tidal volume, cardiac output, relative cardiac output, and absolute cardiac stroke volume.

FIG. 12 shows intraabdominal pressure, respiratory wave pressure, and cardiac pressure schematically arrayed as a two dimensional plot of pressure (mm Hg on a logarithmic scale vs. frequency (Hz). It can be seen that there is an inverse relationship between pressure and frequency, and the various physiologic pressure-related parameters occupy distinct sectors when arrayed in this manner. It is by the distinctness of these profiles that embodiments of the method, as disclosed herein, can resolve a single overall chronological pressure profile into the distinct subprofiles, in accordance with their physiologic origin.

Expandable pressure sensing balloons, per embodiments of the technology, may assume one of at least two basic forms, type 1 or type 2. In balloon embodiments of type 1, which may be generally likened to a conventional party balloon, the pressure-sensing balloon is formed from or includes a compliant or elastic membrane. Accordingly, the surface area of the membrane expands or contracts as a function of the expansion of the balloon. The elasticity of the membrane determines various features of the balloon, as a whole, at different levels of expansion. Upon expansion, the balloon, if unconstrained, maintains a substantially constant or preferred form or shape, as determined by the mandrel upon which the balloon is formed. Upon expansion of the balloon from a minimal volume to its maximal volume, the membrane of the balloon maintains a level of tautness. Within the limits of elasticity of the compliant membrane, an increase in pressure during inflation results in a consequent expansion of volume. The balloon, on the whole may be considered partially compliant in that its shape responds to spatial constraints that it may encounter upon expansion or inflation, however the balloon does have a preferred or native shape, and such shape preference prevents a level of shape compliance or conformability such as that shown by a balloon of type 2.

In balloon embodiments of type 2, the expandable pressure-sensing balloon is formed from or includes a non-compliant, or non-elastic membrane, or a membrane that is substantially non-compliant or non-elastic. Accordingly, the surface area of the membrane does not expand or contract in accordance with the level of balloon expansion. Type 2 pressure-sensing balloons may be generally likened to a conventional Mylar® balloon. The inelasticity of the membrane determines various features of the balloon, as a whole, at different levels of expansion. Upon expansion of the balloon from a minimal volume to a level near its maximal volume, the membrane of the balloon is supple, and has a level of slackness. Expansion of a type 2 balloon occurs by way of outwardly directed smoothing of wrinkles and folds in the membrane. Deflation or compression of a type 2 balloon occurs by way of generally inwardly directed wrinkling and infolding. When a type 2 balloon is fully inflated (or substantially inflated) without being in a confining space, it assumes a preferred or native shape as determined by the geometry of the membrane or fabric of the balloon. However, in a state of partial inflation, the balloon, as a whole, is highly supple and conformable, broadly taking the shape as may be dictated by a confining space.

Expandable pressure sensing balloons, per embodiments of the technology, may also include features of both of the two basic forms, type 1 or type 2. In these embodiments, the membrane may include regions that are elastic (like type 1) and regions that are inelastic (like type 2). A balloon of this hybrid type would, as a whole, behave in a manner drawing from behavioral aspects of both type 1 and type 2 balloons, as described above. Further, type 1 balloons may be formed with a membrane that is not of a homogeneous composition or thickness. In such embodiments, regions of different thickness or composition could have varying degrees of elasticity, thus affecting the behavior of these regions during expansion of the balloon. In still other embodiments, elasticity of the membrane may have a bias or polarity that tends to permit elasticity in one or more directions, and tends to disallow elasticity in one or more other directions.

An aspect of the disclosed technology that is particularly advantageous in achieving a high resolution signal from which pressure profiles from particular physiologic sources (such as peritoneal pressure, respiratory rate, and cardiac rate, relative pulmonary tidal volume, cardiac output, relative cardiac output, and absolute cardiac stroke volume) may be monitored relates to adjusting and maintaining a balance of pressure on either side of the pressure interface represented by the membrane of the pressure sensing balloon. This balance of pressure may be referred to as a pressure differential of zero, or as a zero pressure gauge. Pressure impinging on the external face of balloon (facing the internal aspect of the bladder) is subject to change according to the physiology of the patient. Pressure on the internal face of the balloon (which is in fluid communication with the fluid column) is subject to degradation because of fluid leakage and imperfect seals.

Upon first insertion of the Foley type catheter, external pressure is typically applied to the fluid column and against the pressure interface to a first approximation of pressure being exerted on the pressure interface from within the bladder. Pressure signals, as measured across a pressure interface, have a maximal amplitude when the pressure differential is zero. Accordingly, the amplitude of a pressure signal can be used to tune the pressure being applied from the fluid column against the pressure interface. This process of applying an appropriate amount of pressure against the interface may be referred to as priming the fluid column or priming the balloon. Inasmuch as pressures on either side of the pressure interface may change, as described above, the fluid column may need to be reprimed or re-tuned, from time to time. The necessity of repriming can be monitored by testing small changes in pressure so as to achieve maximal amplitude of a pressure signal profile.

Embodiments of the disclosed system and method include automatic pressure tuning by a controller. Accordingly, the tuning system can detect the optimum target pressure and volume to inflate the balloon by monitoring sensed pressure signals and adding or removing air volume as needed. For example, upon insertion of the catheter, a pressure tuning circuit that regulates the balloon volume and pressure will inflate the balloon until it detects a physiologic-sourced pressure rate. Upon sensing that rate, the pressure tuning controller will add or subtract minute amounts of air in a routinized sequence until the amplitude of the sensed wave is greatest. The control feedback loop between the optimally tuned pressure (manifesting as balloon pressure and volume) and the sensed physiologic pressure profile iterates continuously and or as needed to ensure high fidelity measurement of the physiologic data. In some embodiments, automatic pressure tuning may be performed in the apparent background while the physiologic data is being transmitted and displayed; in other embodiments the system may suspend transmission of physiologic data during a pressure tuning sequence.

Embodiments of the disclosed technology include a gas delivery system that can deliver gas in a priming operation, whereby pressure can be applied to a fluid column proximal to the proximal-facing aspect of the pressure interface. A source of gas, such as compressed air or liquid is held in a storage tank. Using $CO_2$ as an example, $CO_2$ is controllably released from the storage tank through a pressure regulator that can step pressure in the tank (for example, pressure of about 850 psi) down to the range of about 1 psi to about 2 psi. Released gas passes through a filter and a pressure relief valve set at about 2.5 psi. The pressure relief valve is a safety feature that prevents flow through of gas at a level greater than 2.5 psi in the event of failure of the upstream regulator. $CO_2$ exiting the pressure relief valve next passes through a first solenoid-controlled fill valve to enter the catheter line, ultimately filling the balloon that comprises the pressure-sensing interface. Pressure within the balloon is allowed to rise to a level as high as 30 mm Hg, whereupon the first solenoid-controlled valve closes. A second solenoid-controlled valve, distal to the first valve operates as a drain valve, which can release pressure from the catheter to a target pressure. Alternatively, the drain valve may be activated until a respiratory waveform is detected after which the balloon will be optimally primed and the valve will be closed. The drain valve may be subject to proportional control, operably based on voltage or pulse-width modulation (PWM), which allows a drain rate sufficiently slow that the target pressure is reached and the valve can be closed prior to overshoot. Alternatively, a peristaltic or other air pump may be utilized to fill the balloon with room air.

Intrabdominal pressure or bladder pressure, as sensed by an embodiment of the disclosed technology, may also be used to detect the level of patient movement (as may vary, for example, between substantially no movement to a high level of movement) and to report the movement level to a healthcare provider. A short burst of peaks and valleys in bladder pressure activity can serve as a proxy for body movement in that such a bladder pressure profile is a strong indicator that the patient is using their abdominal muscles, as, for example, to sit up or get out of bed. This embodiment may be of particular benefit for patients that are at risk of falling. In a patient that is a fall-risk, a healthcare provider may be notified that the patient is sitting up and respond accordingly. Alternatively, the device may be used to report inactivity of a patient and/or lack of patient movement.

Embodiments of the technology may also report patient movement in the detection or diagnosis of seizure disorder. In this embodiment, the pressure variations may trigger an EEG or recording equipment to allow for intense period of monitoring during an episode suspected of being a seizure. In addition, or alternatively, a pressure sensor, acoustic sensor or other sensors may be used to detect bowel activity, patient movement, seizure activity, patient shivering, frequency of coughing, severity of coughing, sleep quality, speech detection, patient compliance (movement or lack thereof), and may alert the healthcare provider that the patient has not moved and must be turned or rolled. This movement-related information may also be relayed to a hypothermia device, a drug delivery device or other device to control or mitigate seizure activity, shivering and/or coughing.

Embodiments of the technology may also automatically adjust intravenous fluid or drug infusion rates based on feedback from the cardiac output or respiratory rate sensed. In one such embodiment, a patient-controlled analgesia pump may be deactivated if a respiratory rate drops too low. Respiratory depression can be fatal in this group and this safeguard would prevent overdose. An automated feedback system may also be advantageous in a large volume resuscitation procedure, wherein fluid infusion can be tailored based on intraabdominal pressure to prevent abdominal compartment syndrome by sounding an alert and slowing infusion rates as the intraabdominal pressure rises. Yet another automated feedback feature may provide direct feedback to a ventilator system to provide the optimal pressure of ventilated gas. In the setting of increased abdominal pressure, typical ventilator settings do not provide sufficient respiration for the patient. An automated adjustment of the ventilator settings based on intraabdominal pressure feedback from this embodiment may advantageously provide for optimal patient ventilation. Embodiments of the technology may also be applied as a correction in the application or understanding of other diagnostic measurements. For example, central venous pressure may be dramatically distorted in the setting of elevated intraabdominal pressure. Providing direct access to these data by the central venous pressure reporting system allows for the automatic correction and accurate reporting of this critical physiologic parameter. Embodiments of the technology may also be used in a variety of other ways to automate therapy including infusion of fluids that may further include active agents, such as pressors or diuretics in response to increased or decreased cardiac output.

In some embodiments, the Foley type catheter is configured to report the presence of a water droplet or other obstruction in an air-filled lumen, and then handle or resolve the droplet. In a hypothermic setting, in particular, moisture in an air lumen can condense and form obstructive water droplets. Water droplets in an air-filled lumen (or air bubbles in a water-filled lumen) can disturb or complicate pressure signals due to the surface tension of the water. Accordingly, a pressure-transmission lumen in some embodiments of the disclosed technology may include a hydrophilic feature (such as a coating on the wall of the lumen itself, or a hydrophilic fiber running the length of the lumen) to wick moisture away from the lumen in order to maintain a continuous, uninterrupted air channel. In some embodiments, a hygroscopic composition (silica gel, for example) may be used in line with the air infusion line or within the air infusion lumen itself to capture water or humidity. In some embodiments, a hygroscopic composition may be included within the catheter so that the air infusion circuit need not be serviced to replace this material.

In some embodiments of the disclosed technology, air may also be intermittently (and automatically) infused and extracted into the pressure-sensing balloon so that the balloon is in a constant state of being optimally primed, as described in further detail above. In the case of the wicking fiber or hydrophilic coating in the lumen, the air extraction may also contribute to removing and trapping any water from the air line. In the instance of a liquid-filled lumen, a hydrophilic fiber or a hydrophilic coating on the inside of the pressure lumen will provide similar benefit in allowing this lumen to handle an air bubble. In this instance, an air bubble may distort the signal, but the air water interface surface tension is defused by a hydrophilic coating in the lumen of the catheter.

Additionally, a custom extrusion and lumen shape may also be used to prevent obstruction in the case of liquid and/or air-filled lumens. In some embodiments of the technology, for example, a Foley type catheter may have a lumen that is stellate in cross sectional profile. Such a lumen is generally immune from obstruction by a water droplet, as the droplet tends to cohere to itself and push away from the hydrophobic walls. This behavior tends to disallow filling of a cross-sectional space, and allows for an air channel to remain patent around the water droplet and communicate to the sensor. The same logic applies to an air bubble in water in a hydrophilic, stellate water lumen. In this instance the hydrophilic liquid will cling to the walls and allow for a continuous water column that excludes the air bubble to the center of the lumen. The same applies for a hydrophobic liquid in a hydrophobic lumen. In some embodiments, the catheter may include an air channel, and a sensor incorporated within the catheter itself or a fluid lumen that is capable of transmitting the pressure back to a sensor.

In some embodiments, the sensing Foley catheter may include a blood pressure sensing element that may take any of several forms. In one embodiment, a blood pressure sensing element includes a pressure delivery balloon 32 (either a separate, dedicated balloon or a balloon in fluid communication with a device retention balloon or a pressure sensing balloon) that can be optically analyzed as it is inflated to determine at which pressure the vessels within the bladder or urethra are blanched and blood flow is stopped. This approach provides a reading of the perfusion pressure of the tissue abutting the pressure delivery balloon, such reading reflective of both the systemic blood pressure and vascular resistance. This embodiment of a perfusion pressure device may be used to provide early detection or monitoring of a variety of acute or emergent medical conditions such as sepsis, shock, hemorrhage, and can be particularly advantageous in detecting these conditions at an early stage.

Other modalities may be used to detect that the tissue has been blanched or ischemic, as well, with the common methodological aspect being that of the intermittent inflation within the lumen, body cavity or bodily tissues to provide the compression of the vasculature. Embodiments of this device and associated methods may also be used to detect perfusion pressure in other areas of the body with an intermittently inflatable member and optical detection of blood flow or the presence of blood.

Tissue perfusion information may also be provided by way of sensors disposed on the shaft of the catheter such that they contact the urethral wall when the catheter is in place. These sensing technologies may include microdialysis, pyruvate, lactate, $pO_2$, $pCO_2$, pH, perfusion index, near-infrared spectroscopy, laser Doppler flowmetry, urethral capnography, and orthogonal polarization spectroscopy. Any of these tests may also be performed on the urine or the bladder wall itself to generate measurements of tissue perfusion.

Figure 9:
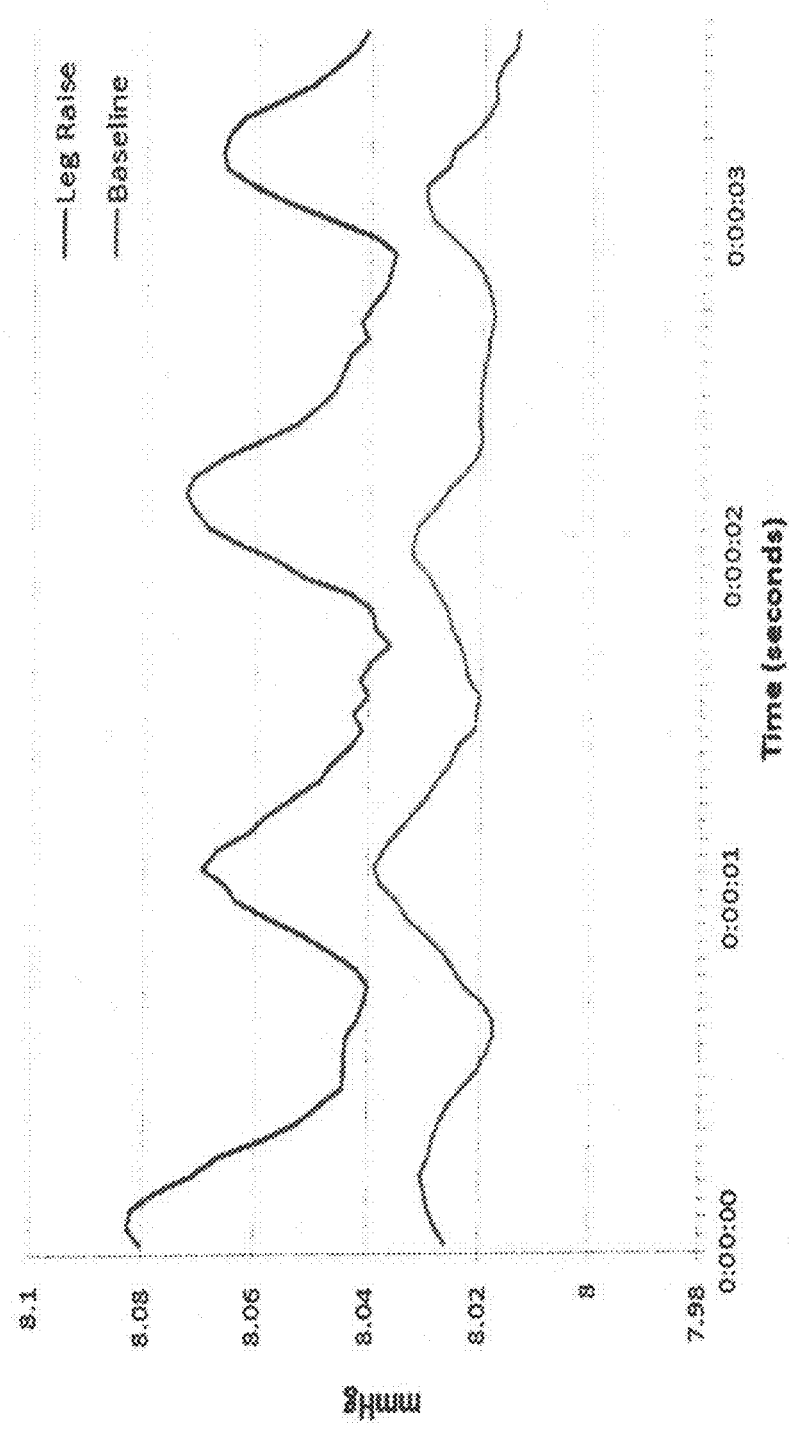
FIG. 9 shows data related to relative cardiac output sensing in a human leg raising exercise in which cardiac output increases, as demonstrated by an increased amplitude of the cardiac pulse.
Figure 10:
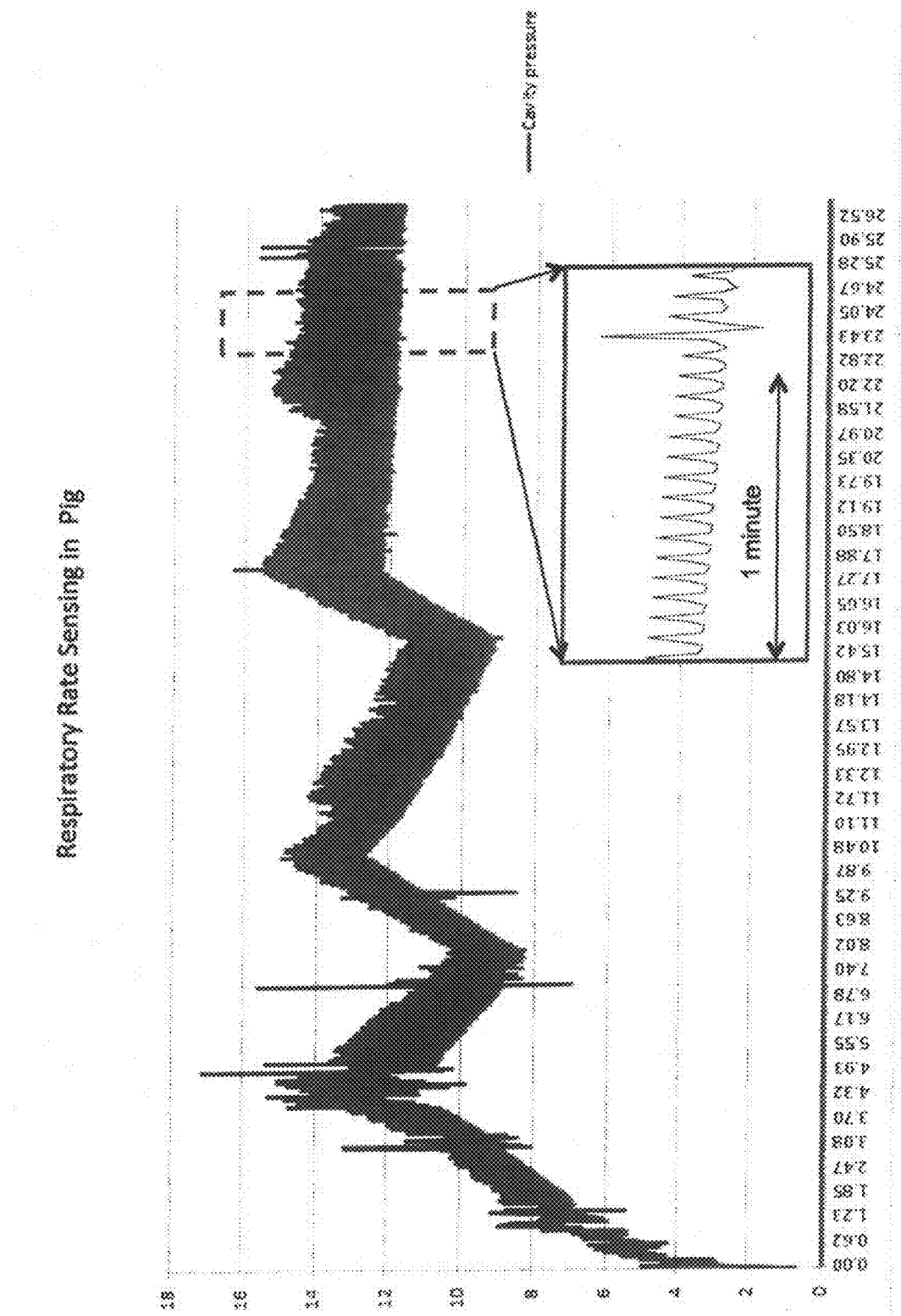
FIG. 10 shows an example of peritoneal sensing data, with a focus on respiratory rate from a pig, as provided by an embodiment of the sensing Foley catheter system.
Figure 11:
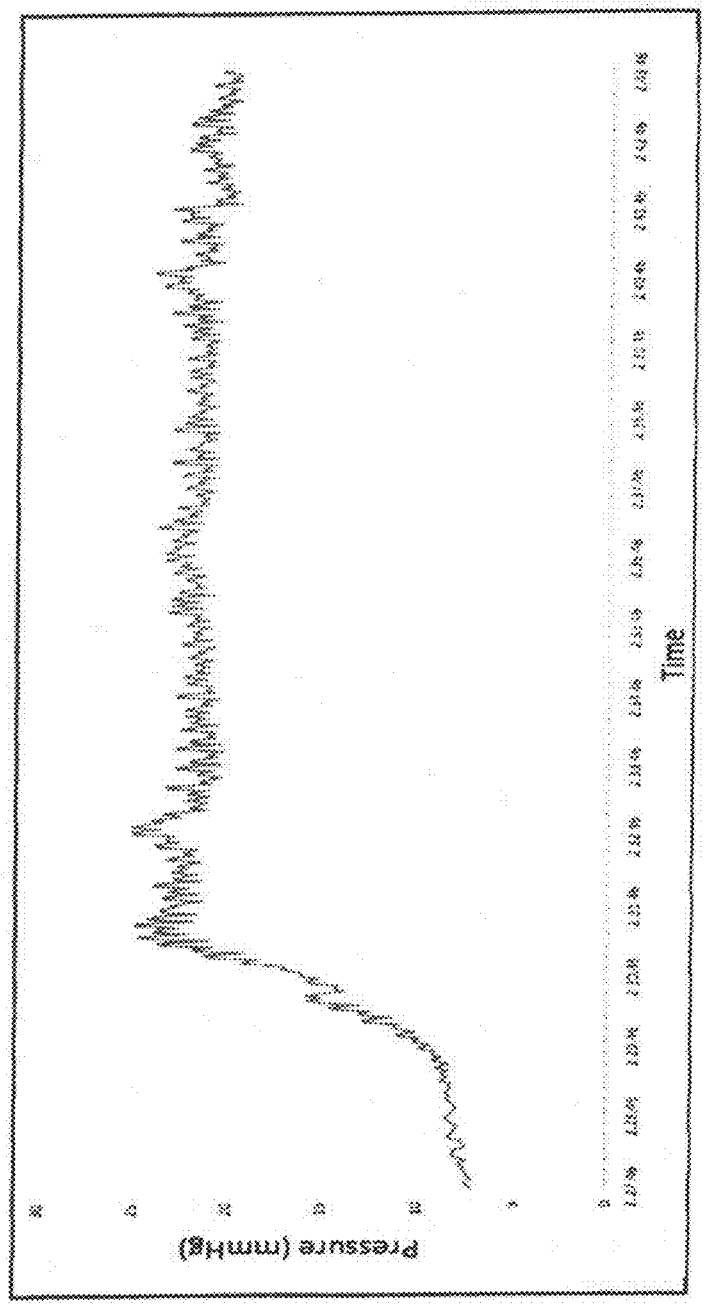
FIG. 11 shows an example of pig study that demonstrates the capability of an embodiment of the sensing Foley catheter system to detect intra-abdominal hypertension.

Embodiments of a sensing Foley catheter have been used to collect data from a human subject (FIGS. 7-9) and from a pig (FIGS. 10-11). The human subject was a consenting and well-informed volunteer.

Figure 7A:
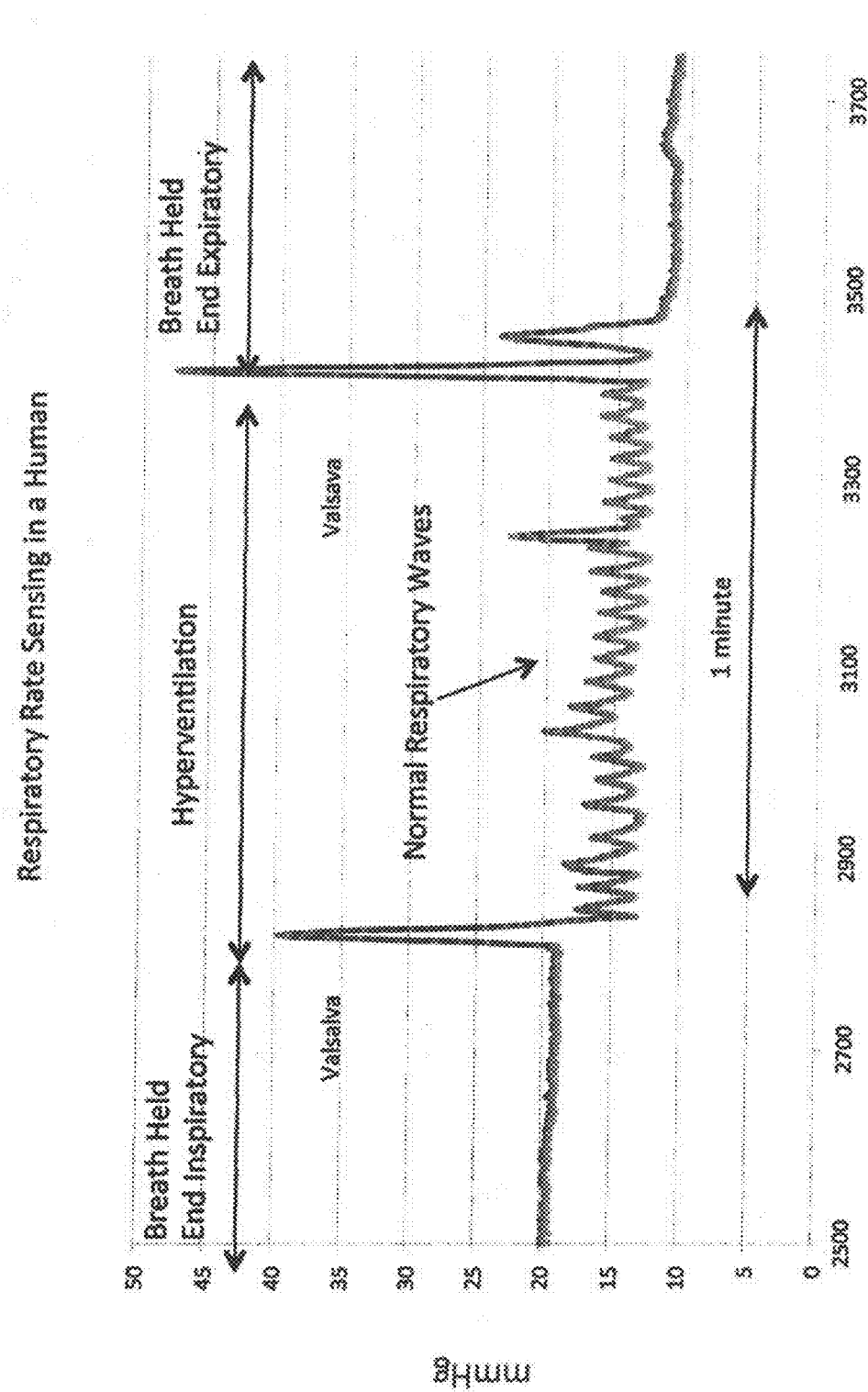
FIG. 7A shows an example of respiratory rate sensing data from a human subject, as provided by an embodiment of the sensing Foley catheter system. During this test period, the subject performs a respiratory sequence as follows: (1) breath being held at the end of an expiration, (2) valsalva, (3) normal respiration, (4) valsalva, and (5) breath being held at the end of an expiration.

FIG. 7A shows an example of respiratory rate sensing data from a human subject, as provided by an embodiment of the sensing Foley catheter system. During this test period, the subject performs a respiratory sequence as follows: (1) breath being held at the end of an expiration, (2) valsalva, (3) normal respiration, (4) valsalva, and (5) breath being held at the end of an expiration. FIG. 7B shows a detailed portion of the respiratory profile of FIG. 8A, a portion of the period of normal respiration.

FIG. 8 shows an example of cardiac rate and relative cardiac output sensing data from a human subject, as provided by an embodiment of the sensing Foley catheter system, and an EKG trace as measured simultaneously and independently.

FIG. 9 shows data related to relative cardiac output sensing in a human leg raising exercise in which cardiac output increases, as demonstrated by an increased amplitude of the cardiac pulse.

The data shown in FIGS. 10 and 11 were derived from studies done with Yorkshire pigs under IACUC-approved protocols. FIG. 10 shows an example of peritoneal sensing data, with a focus on respiratory rate from a pig, as provided by an embodiment of the sensing Foley catheter system. FIG. 11 shows an example of pig study that demonstrates the capability of an embodiment of the sensing Foley catheter system to detect intra-abdominal hypertension. In this study, the peritoneal cavity was accessed with a 5 mm Tenamian trocar. The trocar was then attached to a 5 L bag of Lactated Ringers solution via a peristaltic pump, and the solution was infused at a rate of about 1 L per minute. Fluid flow was discontinued once a pressure of about 20 mmHg was obtained after which there was no net fluid flow in or out of the cavity.

FIG. 13 provides a flow diagram of an embodiment of the method of monitoring pressure as it occurs dynamically as waves of varied frequency and amplitude in the intraabdominal cavity, as detected from within the urinary bladder. Through the agency of a pressure interface, a high fidelity pressure profile is generated and transmitted proximally through a fluid column. More proximally, a pressure transducer converts the high fidelity pressure wave into a high fidelity electrical signal that is informative of pressure frequency and amplitude. The generated high fidelity electrical signal is then processed to yield data subsets that are reflective of components within the overall pressure profile, such subsets being attributable to particular physiologic sources, such as peritoneal pressure, respiratory rate, cardiac rate, relative cardiac output, and patient motion or activity.

Unless defined otherwise, all technical terms used herein have the same meanings as commonly understood by one of ordinary skill in the medical arts. Specific methods, devices, and materials are described in this application, but any methods and materials similar or equivalent to those described herein can be used in the practice of the present invention. While embodiments of the invention have been described in some detail and by way of illustrations, such illustrations are for purposes of clarity of understanding only, and are not intended to be limiting. Various terms have been used in the description to convey an understanding of the invention; it will be understood that the meaning of these various terms extends to common linguistic or grammatical variations thereof. Further, while some theoretical considerations may have been advanced in furtherance of providing an understanding of the technology, the appended claims to the invention are not bound by such theory. Moreover, any one or more features of any embodiment of the invention can be combined with any one or more other features of any other embodiment of the invention, without departing from the scope of the invention. Still further, it should be understood that the invention is not limited to the embodiments that have been set forth for purposes of exemplification, but is to be defined only by a fair reading of claims appended to the patent application, including the full range of equivalency to which each element thereof is entitled.

The invention claimed is:

1. A system for sensing physiologic data from a urinary tract of a patient comprising:
   a Foley type catheter comprising a pressure sensor having a pressure balloon disposed at a distal end of the catheter;
   a pressure transducer in fluid communication with a proximal end of the catheter:
   a fluid column disposed between the pressure balloon and the pressure transducer;
   a fluid delivery system in fluid communication with the fluid column:
   a retention balloon disposed at a distal end of the Foley type catheter between the pressure balloon and the pressure transducer, wherein the retention balloon is separate from the pressure sensor: and
   a urine receptacle in fluid communication with the catheter, wherein the urine receptacle is configured to measure a volume of urine output from the patient;
   wherein the catheter is configured to be inserted into the urinary tract such that the distal end is residing in the bladder,
   wherein the pressure transducer is configured to transduce pressure impinging on the pressure transducer from the pressure balloon into a chronological pressure profile having a resolution that enables processing of the chronological pressure profile into distinct physiologic profiles,
   a controller in communication with the pressure transducer and the urine receptacle configured to process the chronological pressure profile into the distinct physiologic pressure profiles, which include peritoneal pressure, respiratory rate and cardiac output,
   wherein the controller is configured to automatically adjust a pressure exerted within the pressure balloon by adding or removing fluid via the fluid delivery system from the fluid column through the proximal end of the catheter until the pressure exerted within the balloon equilibrates with a baseline of the chronological pressure profile, and
   wherein the controller is configured to receive patient-specific data from a source external to the Foley type catheter and is further configured to integrate the received patient-specific data with the distinct physiologic pressure profiles.

2. The system of claim 1 wherein the pressure transducer is configured to sample the chronological pressure profile at a frequency of at least 5 Hz, wherein the controller in communication with the pressure transducer is configured to process the chronological pressure profile, wherein the processing of the controller has a resolution to yield a relative pulmonary tidal volume profile.

3. The system of claim 1 wherein the pressure transducer is configured to sample the chronological pressure profile at a frequency of at least 5 Hz, and wherein the controller in communication with the pressure transducer is configured to process the chronological pressure profile, wherein the processing of the controller has a resolution to yield physiologic pressure profiles selected from a group consisting of relative cardiac output, and absolute cardiac stroke volume.

4. The system of claim 1 wherein the fluid comprises a gas.

5. The system of claim 1 wherein the fluid comprises a liquid.

6. The system of claim 1 wherein the pressure balloon comprises an expandable balloon.

7. The system of claim 1 further comprising a temperature sensor to monitor a body core temperature of the patient.

8. The system of claim 1 further comprising an analyte sensor.

9. The system of claim 8 wherein the analyte sensor is able to sense an analyte selected from a group consisting of pH, a gas, an electrolyte, a metabolic substrate, a metabolite, an enzyme, or a hormone.

10. The system of claim 1 wherein the pressure transducer is configured to sample the chronological pressure profile at a sampling rate and the controller further resolves the chronological pressure profile into relative pulmonary tidal volume, relative cardiac output, or absolute cardiac stroke volume.

11. The system of claim 1 further comprising a docking station in communication with the urine receptacle, wherein the docking station is configured for data transmission to the controller regarding the volume of urine output detected in the urine receptacle.

12. The system of claim 1 wherein the controller is configured to trigger an alert if the detected volume of urine output is above or below a preset range over a set period of time.

13. The system of claim 1 wherein the physiologic pressure profiles further include at least one of relative pulmonary tidal volume, relative cardiac output, or absolute cardiac stroke volume.

14. A system for sensing physiologic data from a urinary tract of a patient comprising:
  a Foley type catheter comprising a pressure sensor and a temperature sensor, wherein the pressure sensor comprises a pressure balloon disposed at a distal end of the catheter;
  a pressure transducer in fluid communication with a proximal end of the catheter; a fluid column disposed between the pressure balloon and the pressure transducer;
  a fluid delivery system in fluid communication with the fluid column;
  a retention balloon disposed at a distal end of the Foley type catheter between the pressure balloon and the pressure transducer, wherein the retention balloon is separate from the pressure sensor, and wherein, the catheter is configured to be inserted into the urinary tract such that the distal end is residing in the bladder, wherein the pressure transducer is configured to transduce pressure impinging on the pressure transducer from the fluid column into physiologic data comprising a chronological pressure profile having a resolution that enables processing of the chronological pressure profile into distinct physiologic profiles;
  a urine receptacle in fluid communication with the catheter, wherein the urine receptacle is configured to measure a volume of urine output from the patient;
  a controller apparatus in communication with the pressure transducer and the urine receptacle and capable of acquiring the physiological data, wherein the controller apparatus is configured to process the chronological pressure profile into the distinct physiologic pressure profiles, which include peritoneal pressure, respiratory rate and cardiac rate;
  wherein the controller apparatus is configured to automatically adjust a pressure exerted within the pressure balloon by adding or removing fluid via the fluid delivery system from the fluid column through the proximal end of the catheter until the pressure exerted within the balloon equilibrates with a baseline of the chronological pressure profile, and
  wherein the controller is configured to receive patient-specific data from a source external to the Foley type catheter and is further configured to integrate the received patient-specific data with the distinct physiologic pressure profiles.

15. The system of claim 14, wherein the pressure transducer is operable to sample pressure impinging on the pressure transducer at a rate of at least 5 Hz.

16. The system of claim 14 wherein the fluid comprises a gas.

17. The system of claim 14 further comprising a docking station in communication with the urine receptacle, wherein the docking station is configured for data transmission to the controller regarding the volume of urine output detected in the urine receptacle.

18. The system of claim 14 wherein the controller is configured to trigger an alert if the detected volume of urine output is above or below a preset range over a set period of time.

19. The system of claim 14 wherein the physiologic pressure profiles further include at least one of relative pulmonary tidal volume, relative cardiac output, or absolute cardiac stroke volume.

20. A system for sensing physiologic data from a urinary tract of a patient comprising:
  a Foley type catheter comprising sensing elements, said sensing elements comprising a pressure sensor having a pressure interface, a temperature sensor, and one or more analyte sensors;
  a fluid delivery system in fluid communication with a fluid column;
  wherein the pressure sensor comprises a pressure balloon disposed at a distal end of the catheter, a pressure transducer in fluid communication with a proximal end of the catheter, the fluid column disposed between the pressure balloon and the pressure transducer, and a retention balloon disposed at a distal end of the Foley type catheter between the pressure balloon and the pressure transducer, wherein the retention balloon is separate from the pressure sensor, and wherein, the catheter is configured to be inserted into the urinary tract such that the distal end is residing in the bladder, wherein the pressure transducer is configured to transduce pressure impinging on the pressure transducer from the fluid column into physiologic data comprising a chronological pressure profile having a resolution that enables processing of the chronological pressure profile into distinct physiologic profiles;

a urine receptacle in fluid communication with the catheter, wherein the urine receptacle is configured to measure a volume of urine output from the patient; and a controller apparatus in communication with the pressure transducer and the urine receptacle so as to be able to acquire the physiological data, wherein the controller apparatus is configured to process the chronological pressure profile into the distinct physiologic pressure profiles, which include peritoneal pressure, respiratory rate and cardiac output, wherein the controller apparatus is further configured to acquire and process signals from the one or more analyte sensors and to acquire and process signals from the temperature sensor; and wherein the controller apparatus is configured to automatically adjust a pressure exerted within the pressure interface by adding or removing fluid via the fluid delivery system from the fluid column through the proximal end of the catheter the pressure exerted within the balloon equilibrates with a baseline of the chronological pressure profile, and wherein the controller is configured to receive patient-specific data from a source external to the Foley type catheter and is further configured to integrate the received patient-specific data with the distinct physiologic pressure profiles.

21. The system of claim 20 wherein the fluid comprises a gas.

22. The system of claim 20 further comprising a docking station in communication with the urine receptacle, wherein the docking station is configured for data transmission to the controller regarding the volume of urine output detected in the urine receptacle.

23. The system of claim 20 wherein the controller is configured to trigger an alert if the detected volume of urine output is above or below a preset range over a set period of time.

24. The system of claim 20 wherein the physiologic pressure profiles further include at least one of relative pulmonary tidal volume, relative cardiac output, or absolute cardiac stroke volume.

* * * * *